United States Patent
Yamanashi et al.

(10) Patent No.: US 10,572,755 B2
(45) Date of Patent: *Feb. 25, 2020

(54) IMAGE ANALYSIS APPARATUS FOR CALCULATING DEGREE OF CHANGE IN DISTRIBUTION CHARACTERISTIC VALUES, IMAGE ANALYSIS SYSTEM, AND METHOD FOR OPERATING IMAGE ANALYSIS SYSTEM

(71) Applicant: OLYMPUS CORPORATION, Tokyo (JP)

(72) Inventors: Momoko Yamanashi, Tachikawa (JP); Tetsuhiro Yamada, Hino (JP); Toshio Nakamura, Hachioji (JP); Ryuichi Toyama, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 15/936,857

(22) Filed: Mar. 27, 2018

(65) Prior Publication Data

US 2018/0218233 A1 Aug. 2, 2018

Related U.S. Application Data

(63) Continuation of application No. PCT/JP2016/077263, filed on Sep. 15, 2016.

(30) Foreign Application Priority Data

Sep. 28, 2015 (JP) .................................. 2015-190134

(51) Int. Cl.
*G06K 9/00* (2006.01)
*G06K 9/32* (2006.01)
(Continued)

(52) U.S. Cl.
CPC ........ *G06K 9/3233* (2013.01); *A61B 1/00009* (2013.01); *A61B 1/05* (2013.01);
(Continued)

(58) Field of Classification Search
CPC .......... G06K 9/3233; A61B 1/05; A61B 1/04; A61B 1/00002; A61B 1/0669;
(Continued)

(56) References Cited

U.S. PATENT DOCUMENTS

2007/0213588 A1 9/2007 Morishita et al.
2009/0208071 A1 8/2009 Nishimura et al.
(Continued)

FOREIGN PATENT DOCUMENTS

JP 2006223376 A 8/2006
JP 2007229054 A 9/2007
(Continued)

OTHER PUBLICATIONS

International Search Report dated Nov. 29, 2016 issued in PCT/JP2016/077263.

*Primary Examiner* — Amir Alavi
(74) *Attorney, Agent, or Firm* — Scully, Scott, Murphy & Presser, P.C.

(57) ABSTRACT

An image analysis apparatus includes a region extraction unit configured to determine, as analysis target regions, respective predetermined regions in a first image and a second image that are acquired at timings before and after execution of a predetermined action to a subject and inputted through an image input unit in a state where an endoscope is continuously inserted in the subject, a distribution characteristic value calculation unit configured to obtain a first distribution characteristic value by extracting a color component of the analysis target region in the first image, and to obtain a second distribution characteristic value by extract- (Continued)

ing a color component of the analysis target region in the second image, and an image analysis unit configured to calculate the degree of change in the second distribution characteristic value with respect to the first distribution characteristic value.

15 Claims, 21 Drawing Sheets

(51) Int. Cl.
*G02B 23/24* (2006.01)
*G06K 9/46* (2006.01)
*G06T 7/254* (2017.01)
*G06T 7/12* (2017.01)
*A61B 1/00* (2006.01)
*G06T 7/13* (2017.01)
*G06T 7/90* (2017.01)
*A61B 1/05* (2006.01)

(52) U.S. Cl.
CPC ............ *G02B 23/24* (2013.01); *G06K 9/4652* (2013.01); *G06T 7/12* (2017.01); *G06T 7/13* (2017.01); *G06T 7/254* (2017.01); *G06T 7/90* (2017.01); *G06K 2209/05* (2013.01)

(58) Field of Classification Search
CPC ... A61B 5/4551; A61B 1/0638; A61B 1/0002; A61B 1/00018; A61B 1/00009; G06T 7/13; G06T 7/90; G06T 1/60; G06T 1/20; G02B 23/24; H04N 5/225
See application file for complete search history.

(56) References Cited

U.S. PATENT DOCUMENTS

| | | | |
|---|---|---|---|
| 2015/0297066 A1* | 10/2015 | Yanagidate | A61B 1/00181 600/109 |
| 2016/0287061 A1* | 10/2016 | Shigeta | A61B 1/0638 |
| 2016/0324398 A1* | 11/2016 | Sasaki | G02B 23/2446 |
| 2017/0358084 A1* | 12/2017 | Yamada | A61B 1/04 |
| 2018/0158223 A1* | 6/2018 | Kobayashi | F01D 21/003 |
| 2018/0218233 A1* | 8/2018 | Yamanashi | A61B 1/00 |
| 2018/0279863 A1* | 10/2018 | Godo | A61B 1/041 |
| 2018/0333045 A1* | 11/2018 | Yamanashi | A61B 1/00009 |

FOREIGN PATENT DOCUMENTS

| | | |
|---|---|---|
| JP | 2010005056 A | 1/2010 |
| WO | 2004104927 A2 | 12/2004 |
| WO | 2006087981 A1 | 8/2006 |
| WO | 2007099840 A1 | 9/2007 |

* cited by examiner

IMAGE ANALYSIS APPARATUS FOR CALCULATING DEGREE OF CHANGE IN DISTRIBUTION CHARACTERISTIC VALUES, IMAGE ANALYSIS SYSTEM, AND METHOD FOR OPERATING IMAGE ANALYSIS SYSTEM

CROSS REFERENCE TO RELATED APPLICATIONS

This application is a continuation application of PCT/JP2016/077263 filed on Sep. 15, 2016 and claims benefit of Japanese Application No. 2015-190134 filed in Japan on Sep. 28, 2015, the entire contents of which are incorporated herein by this reference.

BACKGROUND OF THE INVENTION

1. Field of the Invention

The present invention relates to an image analysis apparatus which analyzes change of a subject from time-sequentially acquired images of the subject, an image analysis system, and a method for operating the image analysis apparatus.

2. Description of Related Art

A variety of technologies are conventionally proposed for analyzing change of a subject from time-sequentially acquired images of the subject.

For example, Japanese Patent Application Laid-Open Publication No. 2010-5056 discloses a technology of an image acquisition apparatus for picking up a normal image of an observation target by means of an image pickup device, and performing a spectrum image process on an image signal outputted from the image pickup device so as to generate a spectral estimation image signal of a predetermined wavelength, wherein: a spectrum image generation unit generates, on the basis of an image signal outputted from the image pickup device, a spectral estimation image signal of a specified wavelength related to a drug to be administered into the observation target such that the spectral estimation image signal serves as a spectral estimation image signal for acquiring luminance information; a luminance information acquisition unit acquires the luminance information of each of spectral estimation image signals for acquiring luminance information generated at a predetermined time interval and acquires the rate of change in the luminance information; and a display device displays an image on the basis of the rate of change rate in the luminance information.

In addition, International Publication No. WO2004/104927 discloses an image analysis method including: picking up a digital image of tooth tissue; determining a first pixel color component value and a second pixel color component value for each of multiple pixels in the digital image; and calculating a first function (e.g., R/G) of the pixel on the basis of the first component value and the second component value.

SUMMARY OF THE INVENTION

An image analysis apparatus according to one aspect of the present invention includes: an image input unit configured to receive an input of a first image of a subject acquired at a first timing and an input of a second image of the subject acquired at a second timing later than the first timing, in a state where an endoscope is continuously inserted in the subject; a region extraction unit configured to determine, as analysis target regions, respective predetermined regions in the first image and the second image acquired at timings before and after execution of a predetermined action to the subject and inputted through the image input unit; a distribution characteristic value calculation unit configured to obtain a first distribution characteristic value by extracting a color component of the analysis target region in the first image, and to obtain a second distribution characteristic value by extracting a color component of the analysis target region in the second image; and an image analysis unit configured to calculate a degree of change in the second distribution characteristic value with respect to the first distribution characteristic value.

An image analysis system according to one aspect of the present invention includes: an endoscope configured to be inserted into a subject and pick up and acquire an image of an inside of the subject; and the image analysis apparatus.

A method for operating an image analysis apparatus according to one aspect of the present invention includes: inputting, to an image input unit, a first image of a subject acquired at a first timing and a second image of the subject acquired at a second timing later than the first timing in a state where an endoscope is continuously inserted in the subject; determining, by a region extraction unit, respective predetermined regions in the first image and the second image as analysis target regions, the first image and the second image being acquired at timings before and after execution of a predetermined action to the subject and inputted through the image input unit; obtaining, by a distribution characteristic value calculation unit, a first distribution characteristic value by extracting a color component of the analysis target region in the first image and obtaining, by the distribution characteristic value calculation unit, a second distribution characteristic value by extracting a color component of the analysis target region in the second image; and calculating, by an image analysis unit, a degree of change of the second distribution characteristic value with respect to the first distribution characteristic value.

DETAILED DESCRIPTION OF PREFERRED EMBODIMENTS

Figure 1:
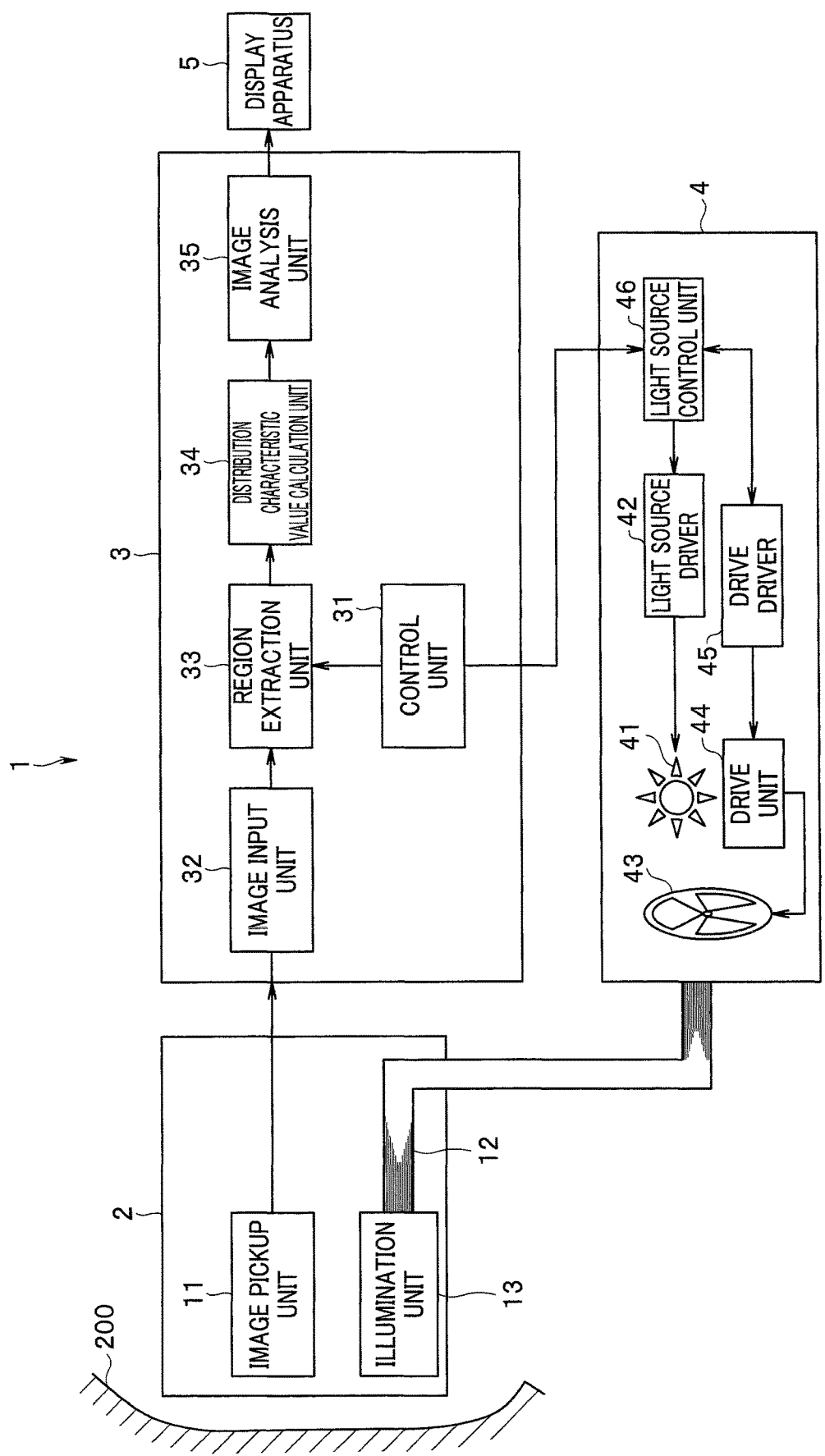
FIG. 1 is a block diagram illustrating the schematic configuration of an image analysis system according to a first embodiment of the present invention.

Hereinafter, embodiments of the present invention are described with reference to the drawings.

Note that the present invention is not limited to the embodiments. Further, components identical to one another are denoted by the same reference numerals in the drawings. Moreover, it should be noted that the drawings are schematic ones, and the relationship between the thickness and the width of each component, the ratio among the respective components, and the like in the drawings are different from actual ones. The dimensions and the ratio throughout the drawings are partially different from one another.

<First Embodiment>

Figure 2:
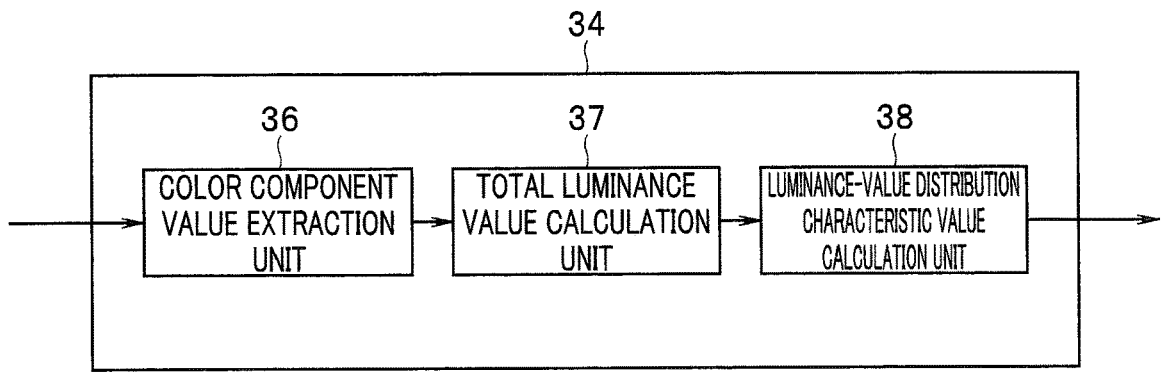
FIG. 2 is a block diagram illustrating the configuration of a distribution characteristic value calculation unit of the image analysis apparatus in the image analysis system according to the first embodiment.
Figure 3:
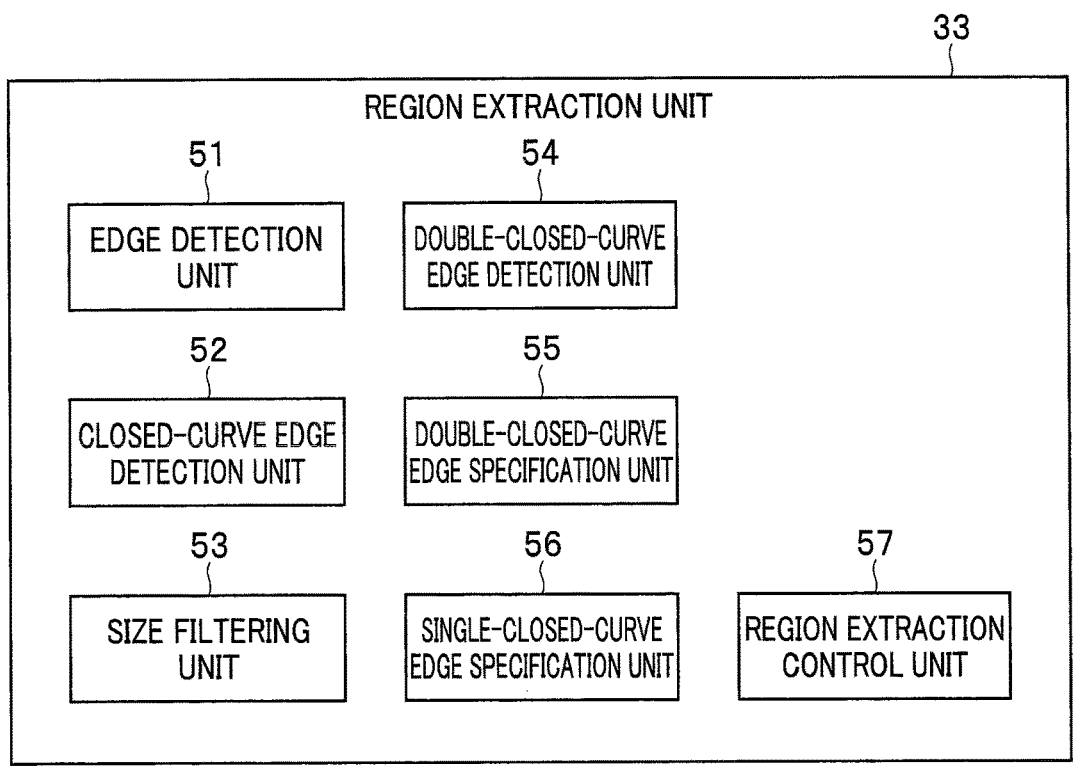
FIG. 3 is a block diagram illustrating the configuration of a region extraction unit of the image analysis apparatus in the image analysis system according to the first embodiment.

FIG. 1 is a block diagram illustrating a schematic configuration of an image analysis system according to a first embodiment of the present invention. FIG. 2 is a block diagram illustrating a configuration of a distribution characteristic value calculation unit of an image analysis apparatus in the image analysis system according to the first embodiment. FIG. 3 is a block diagram illustrating a configuration of a region extraction unit of the image analysis apparatus in the image analysis system according to the first embodiment.

Note that the "image analysis system" and the "image analysis apparatus" are exemplified by an endoscope system and a video processor, respectively, in the embodiments described later.

As illustrated in FIG. 1, an endoscope system 1 as the image analysis system mainly includes an endoscope 2, a video processor 3 as the image analysis apparatus, a light source apparatus 4, and a display apparatus 5.

As the entire system, the endoscope system 1 can support observation with narrow band imaging (NBI) in the present embodiment.

The endoscope 2 includes an insertion section (not illustrated) which is inserted into a subject 200, and further includes an image pickup unit 11 which picks up an image of the subject 200 and acquires an image signal and which is arranged at a distal end portion of the insertion section, a light guide 12 which transmits illumination light from the light source apparatus 4, and an illumination unit 13 which irradiates the subject 200 with the illumination light.

Note that, in order to perform magnification observation with NBI while reducing a noise component, a distal hood, a distal attachment, or the like is attached to the distal end of the endoscope 2.

In the present embodiment, a predetermined load (a predetermined action) is imparted to the subject, and change of the subject is time-sequentially observed over a time period before and after the impartment of the load (the action). To this end, the endoscope 2 is configured to time-sequentially acquire images of the subject.

The "predetermined action" herein refers to administration of a medicinal solution to the subject, for example. Note that the "medicinal solution" in the present embodiment refers to a physiological saline solution, glucose, or liquid fat (e.g., lipid emulsion), for example. As one specific example of the load (the action), scattering of glucose is explained later.

The "predetermined action" is not limited to the aforementioned administration of a medicinal solution, but may be intravenous injection, air feeding to a body cavity, an action of physically bringing a treatment instrument or the endoscope itself into contact with the inside of a body, or the like.

Note that, in order to more precisely get to know change of the subject before and after impartment of the predetermined action to the subject, brightness setting in the endoscope 2 is desirably in the same status. Therefore, images of the subject are preferably acquired while the amount of light emitted from the light source is kept constant without controlling of the light source before and after impartment of the predetermined action to the subject.

The video processor 3 includes a control unit 31 which generally controls the entire endoscope system 1, and an image input unit 32, a region extraction unit 33, a distribution characteristic value calculation unit 34, and an image analysis unit 35 which are controlled by the control unit 31.

Note that, in the present embodiment, the video processor 3 performs a function as a signal processing apparatus for an image pickup signal from the image pickup unit 11 of the endoscope 2, and also serves as the "image analysis apparatus".

Images of the subject time-sequentially acquired by the image pickup unit 11 of the endoscope 2 are inputted to the image input unit 32.

In a first image that is acquired at a first timing and is inputted through the image input unit 32 and a second image that is acquired at a second timing later than the first timing and is inputted through the image input unit 32, the region extraction unit 33 specifies an element of interest (an element of interest in the present embodiment is, for example, an intestinal villus image part which is a feature region, as described later), which is formed of an annular surrounding portion and a center portion surrounded by the surrounding portion and colored in a color different from the color of the surrounding portion, and extracts only the center portion of the element of interest as an analysis target region (a more detailed description is given later).

The distribution characteristic value calculation unit 34 extracts color component values of each of the analysis target region of the first image and the analysis target region of the second image extracted by the region extraction unit 33, and further, calculates respective distribution characteristic values of luminance values concerning the respective total values of the extracted color component values (a more detailed description is given later).

The image analysis unit 35 calculates the degree of change between the distribution characteristic value (a first distribution characteristic value) concerning the analysis target region of the first image calculated by the distribution characteristic value calculation unit 34 and the distribution characteristic value (a second distribution characteristic value) concerning the analysis target region of the second image calculated by the distribution characteristic value calculation unit 34 (a more detailed explanation is given later).

The light source apparatus 4 includes a light source 41, a light source driver 42, a rotary filter 43, a drive unit 44, a drive driver 45, and a light source control unit 46.

The light source 41 is configured by use of a white LED, a xenon lamp, or the like, and generates white light under control by the light source control unit 46. The light source driver 42 causes the light source 41 to emit white light under control by the light source control unit 46. Light emitted from the light source 41 is cast from the illumination unit 13 of the endoscope 2 via the rotary filter 43, a condensing lens (not illustrated), and the light guide 12.

The rotary filter 43 is disposed on the light path of the white light emitted from the light source 41, and is rotated to receive the white light emitted from the light source 41 such that a light supporting observation with NBI, namely, a light narrow-banded so as to include the respective wavelength regions of a blue light the wavelength of which is approximately 415 nm (for example, approximately 400 to 440 nm) and a green light the wavelength of which is approximately 540 nm (for example, approximately 525 to 555 nm), is transmitted through the rotary filter 43. Here, in the normal case of observation with NBI adopted in the present embodiment, blue and green narrow-banded lights are cast onto an intestinal mucous membrane surface. The blue reflection light is converted to blue and green lights and the green reflection light is converted to a red light, so as to be outputted on a monitor.

Under control by the light source control unit 46, the drive driver 45 supplies a predetermined current to the drive unit 44. Under control by the light source control unit 46, the drive unit 44 causes the rotary filter 43 to rotationally operate by using, as a reference, a synchronization signal transmitted from the video processor 3.

The display apparatus 5 has a function of receiving, from the video processor 3 via a predetermined video cable, images of the subject, etc. generated by the video processor 3 and displaying the images. Note that, in addition to images of the subject picked up by the image pickup unit 11 of the endoscope 2, various types of information such as an image arrangement display 61, an image acquisition time display 62, and an image arrangement order display 63 which will be described later can be displayed in the present embodiment.

<Distribution Characteristic Value Calculation Unit 34>

Next, the configuration of the distribution characteristic value calculation unit 34 is described with reference to FIG. 2.

As illustrated in FIG. 2, the distribution characteristic value calculation unit 34 includes a color component value extraction unit 36, a total luminance value calculation unit 37, and a luminance-value distribution characteristic value calculation unit 38.

The color component value extraction unit 36 extracts respective color component values (R, G, B component values) of each analysis target region of the first image extracted by the region extraction unit 33, and also extracts respective color component values (R, G, B component values) of each analysis target region of the second image.

The total luminance value calculation unit 37 obtains a luminance value (a first total luminance value) concerning the total value of the respective color component values of each analysis target region of the first image extracted by the color component value extraction unit 36, and also calculates a luminance value (a second total luminance value) concerning the total value of the respective color component values of each analysis target region of the second image extracted by the color component value extraction unit 36.

The luminance-value distribution characteristic value calculation unit 38 calculates respective distribution characteristic values (a first distribution characteristic value and a second distribution characteristic value) concerning the respective total luminance values (the first total luminance values and the second total luminance values) calculated by the total luminance value calculation unit 37. Note that, in the present embodiment, the "distribution characteristic value" is obtained as a standard deviation or dispersion.

<Region Extraction Unit 33>

Next, the configuration of the region extraction unit 33 is described with reference to FIG. 3.

The region extraction unit 33 is configured to determine the color difference between the surrounding portion and the center portion, on the basis of at least a hue difference, a saturation difference, or a luminance difference. Therefore, difference in color component values corresponds to the color difference. For example, even a case where the surrounding portion and the center portion are different only in the luminance while being equal to each other in terms of the hue and the saturations, corresponds to the color difference.

As illustrated in FIG. 3, the region extraction unit 33 includes an edge detection unit 51, a closed-curve edge detection unit 52, a size filtering unit 53, a double-closed-curve edge detection unit 54, a double-closed-curve edge specification unit 55, a single-closed-curve edge specification unit 56, and a region extraction control unit 57.

The edge detection unit 51 detects edges by performing edge detection filtering on an image, for example.

Further, the closed-curve edge detection unit 52 detects edges each forming a closed curve from among the edges detected by the edge detection unit 51.

The size filtering unit 53 selects, from among the closed curve edges detected by the closed-curve edge detection unit 52, only closed curve edges the sizes of which fall within the range of such a size that can be taken by an element of interest (for example, within the range of such a size that can be taken as an intestinal villus).

Further, the double-closed-curve edge detection unit 54 detects, from among closed curve edges detected by the closed-curve edge detection unit 52 and further selected, for example, by the size filtering unit 53, a double closed curve edge which forms double edges (that is, which is configured by an outer closed curve edge and an inner closed curve edge inside the outer closed curve edge).

When the color of the region inside the inner closed curve edge of the double closed curve edge detected by the double-closed-curve edge detection unit 54 is different from the color of the region between the inner closed curve edge and the outer closed curve edge, the double-closed-curve edge specification unit 55 specifies the region inside the inner closed curve edge as the center portion.

Moreover, when the color of the region inside the inner closed curve edge falls within a first color range (for example, the first color range is close to red in a case where the element of interest is an intestinal villus) corresponding to the center portion of the element of interest while the color of the region between the inner closed curve edge and the outer closed curve edge falls within a second color range (a color range different from the first color range) (for example, the second color range is close to white in a case where the element of interest is an intestinal villus) corresponding to the surrounding portion of the element of interest, the double-closed-curve edge specification unit 55 specifies the region inside the inner closed curve edge as the center portion.

Note that, as described above, the color difference is determined on the basis of at least a hue difference, a saturation difference, or a luminance difference. Therefore, the color range is determined on the basis of any one of hue, saturation, and luminance, or on the basis of a combination of two or more of hue, saturation, and luminance. For example, the color range may be determined on the basis of the combination of hue and saturation, or the luminance range may be determined as the color range (that is, the center portion and the surrounding portion may be discriminated from each other on the basis of only the luminance). In a case where the element of interest is an intestinal villus and the luminance range is determined as the color range, the first color range may be set to a slightly lower luminance range and the second color range may be set to a luminance range higher than the first color range, for example.

Furthermore, it is more preferable that, only when the size filtering unit 53 determines that the sizes of the inner closed curve edge and the outer closed curve edge fall within respective ranges that can be taken by an element of interest, the double-closed-curve edge specification unit 55 specifies the region inside the inner closed curve edge as the center portion.

In the present embodiment, when the number of the center portions of elements of interest specified by the double-closed-curve edge specification unit 55 is less than a predetermined number (the predetermined number herein is a plural number), more center portions of elements of interest are specified by use of the single-closed-curve edge specification unit 56 (however, the center portions of elements of interest may be specified by use of only the single-closed-curve edge specification unit 56 without involving use of the double-closed-curve edge specification unit 55).

When the colors of the inside and the outside of a closed curve edge detected by the closed-curve edge detection unit 52 are different from each other, the single-closed-curve edge specification unit 56 specifies, as the center portion, the inside of a region surrounded by the closed curve edge.

In the present embodiment, closed curve edges that have been specified as being not targets to be processed by the double-closed-curve edge specification unit 55 undergo the process by the single-closed-curve edge specification unit 56. However, any closed curve edge including three, four, or more edges, which are more than two, is considered to be a double closed curve edge. Accordingly, a target to be proceed by the single-closed-curve edge specification unit 56 is a single closed curve edge.

In addition, when the color of the region inside the single closed curve edge falls within the first color range corresponding to the center portion of an element of interest and the color of a region in the outer vicinity of the single closed curve edge falls within the second color range corresponding to the surrounding portion of an element of interest, the single-closed-curve edge specification unit 56 specifies the region inside the single closed curve edge as the center portion.

It is more preferable that, only when the size filtering unit 53 determines that the size of the single closed curve edge falls within such a range that can be taken by an element of interest, the single-closed-curve edge specification unit 56 specifies, as the center portion, the inside of a region surrounded by the single closed curve edge.

The region extraction control unit 57 controls the respective components in the region extraction unit 33, that is, controls the above-described edge detection unit 51, the closed-curve edge detection unit 52, the size filtering unit 53, the double-closed-curve edge detection unit 54, the double-closed-curve edge specification unit 55, the single-closed-curve edge specification unit 56, and the like to perform operations which are described later with reference to FIGS. 6 to 9.

<Process in Image Analysis System>

Figure 4:
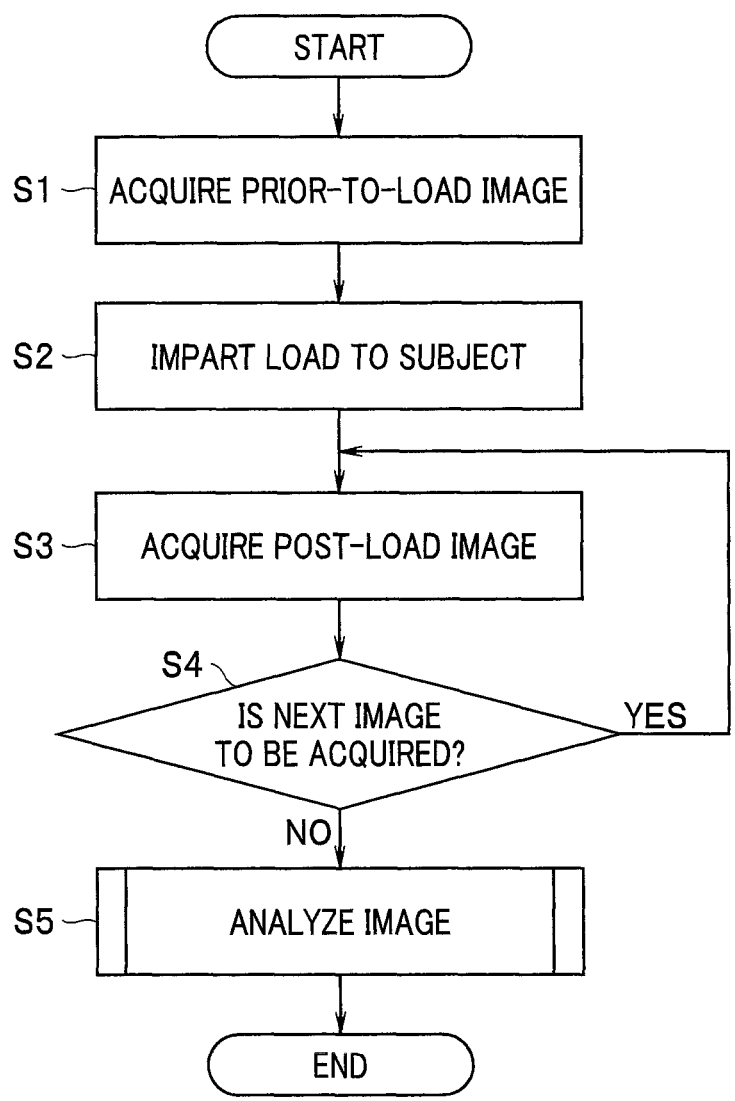
FIG. 4 is a flowchart showing a basic process in the image analysis system according to the first embodiment.

FIG. 4 is a flowchart showing a basic process in the image analysis system.

The process is started under control by the control unit 31 of the video processor 3. First, the control unit 31 controls the endoscope 2 such that an image (a prior-to-load image or the first image) before impartment of the load (the predetermined action) to the subject is acquired through the image pickup unit 11 at the first timing (step S1).

The subject is assumed to be a villus of an intestine (specifically, a small intestine, for example) in the present embodiment (however, the subject is not limited to an intestinal villus, but other examples of the subject include a tongue portion, an esophagus, a gastric mucosa, and a large intestine). Also, when an image of the subject is acquired by the endoscope 2, information about an amount of light emitted at acquisition of the image may be simultaneously stored in the image analysis apparatus (the video processor 3) or in the endoscope 2, for example.

Thereafter, the load (the predetermined action) is imparted to the subject (step S2). As the load (the predetermined action) imparted to the subject at step S2, scattering of glucose is assumed here. Scattering of glucose causes increase of the volume of blood flowing through capillaries. Accordingly, a larger amount of light is absorbed by hemoglobin in the blood. Consequently, an area in the villus where many capillaries are gathered are observed as a dark area.

The load (the predetermined action) to the subject is not limited to scattering of glucose. As described above, for example, the load may be administration of a medicinal solution such as a physiological saline solution, glucose, or liquid fat (e.g., lipid emulsion) to the subject. Moreover, the load is not limited to administration of the medicinal solution, but may be intravenous injection, air feeding to a body cavity, or an action of physically bringing a treatment instrument or the endoscope itself into contact with the inside of the body, or the like.

Subsequently, at the second timing later than the first timing, the control unit 31 picks up and acquires an image (a post-load image, the second image) after impartment of the load through the endoscope 2 in a state where the endoscope 2 is left inserted in the subject (step S3).

Note that, in the present embodiment, when administration of glucose into the subject is performed as one example of the action, observation is time-sequentially continued for about three minutes (180 seconds) after the action.

In a case where information about the amount of emitted light has been stored at step S1, when the image after impartment of the load to the subject is acquired through the endoscope 2, the image is acquired under a condition the same as the condition at step S1 by reference to the information about the amount of emitted light. Note that a function of deleting later the information about the amount of emitted light stored at step S1 may be provided. Acquisition of the information about the amount of emitted light, image acquisition using the information about the amount of emitted light, and deletion of the information about the emitted light amount may be achieved through operation of an operation section of the endoscope 2, operation of a switch provided to a control panel for controlling the image analysis system, or operation of a foot switch for operating the endoscope 2, for example.

The control unit 31 determines whether or not to further acquire a next image (step S4). When a next image is determined to be acquired, the process returns to step S3 to acquire a next post-load image.

When completion of image acquisition is determined at step S4, the control unit 31 performs image analysis by controlling the region extraction unit 33, the distribution characteristic value calculation unit 34, the image analysis unit 35, etc. of the video processor 3 (step S5). After completion of the image analysis, the process is ended.

<Image Analysis in the First Embodiment>

Figure 5:
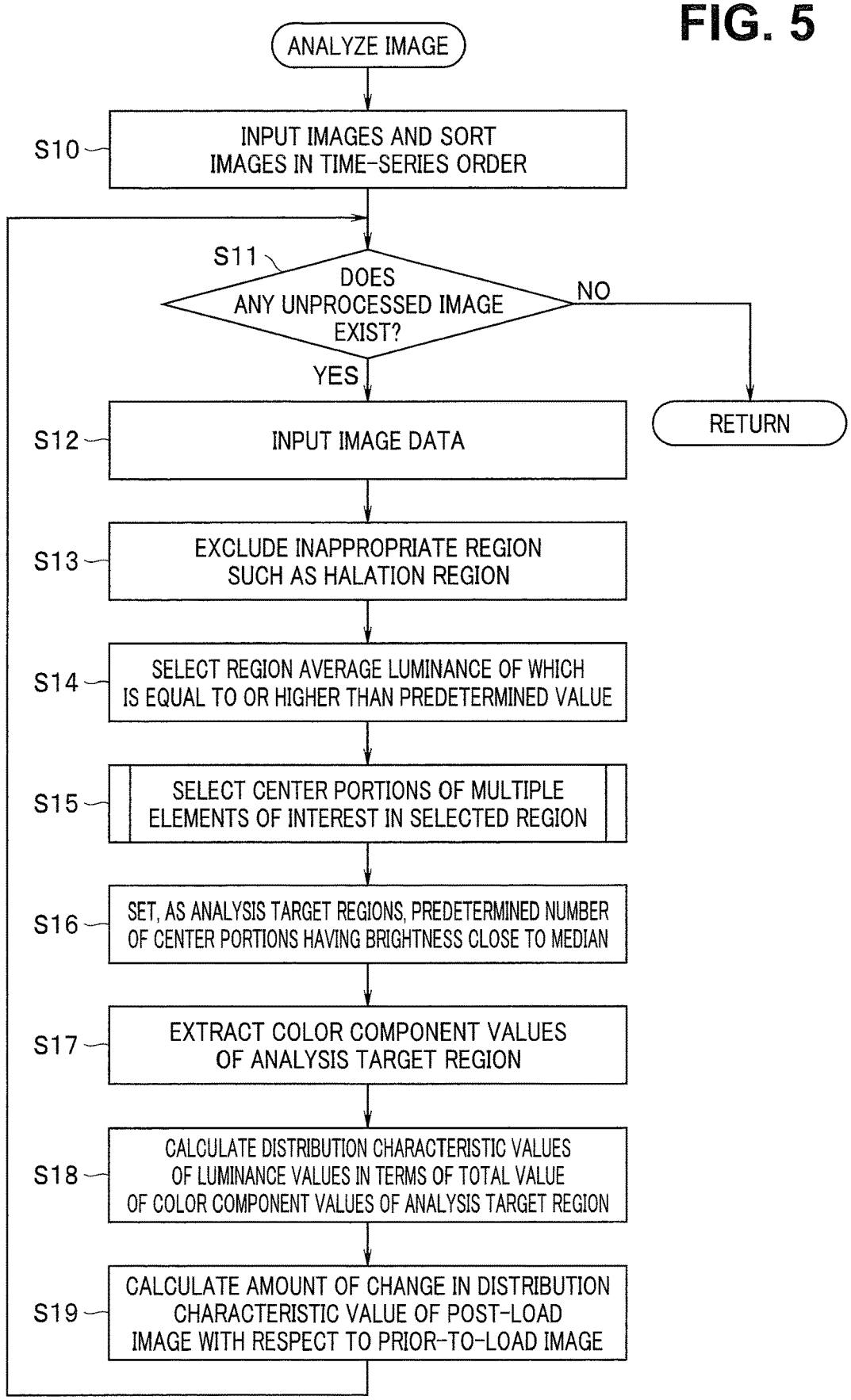
FIG. 5 is a flowchart showing an image analysis process to be executed by the image analysis apparatus in the image analysis system according to the first embodiment.

FIG. 5 is a flowchart showing an image analysis process to be executed by the image analysis apparatus (the video processor 3) in the image analysis system according to the first embodiment.

When this process is started under control by the control unit 31, time-sequentially acquired images of the subject are inputted to the image input unit 32 from the endoscope 2, and the images are sorted in a time-series order (step S10).

Figure 10:
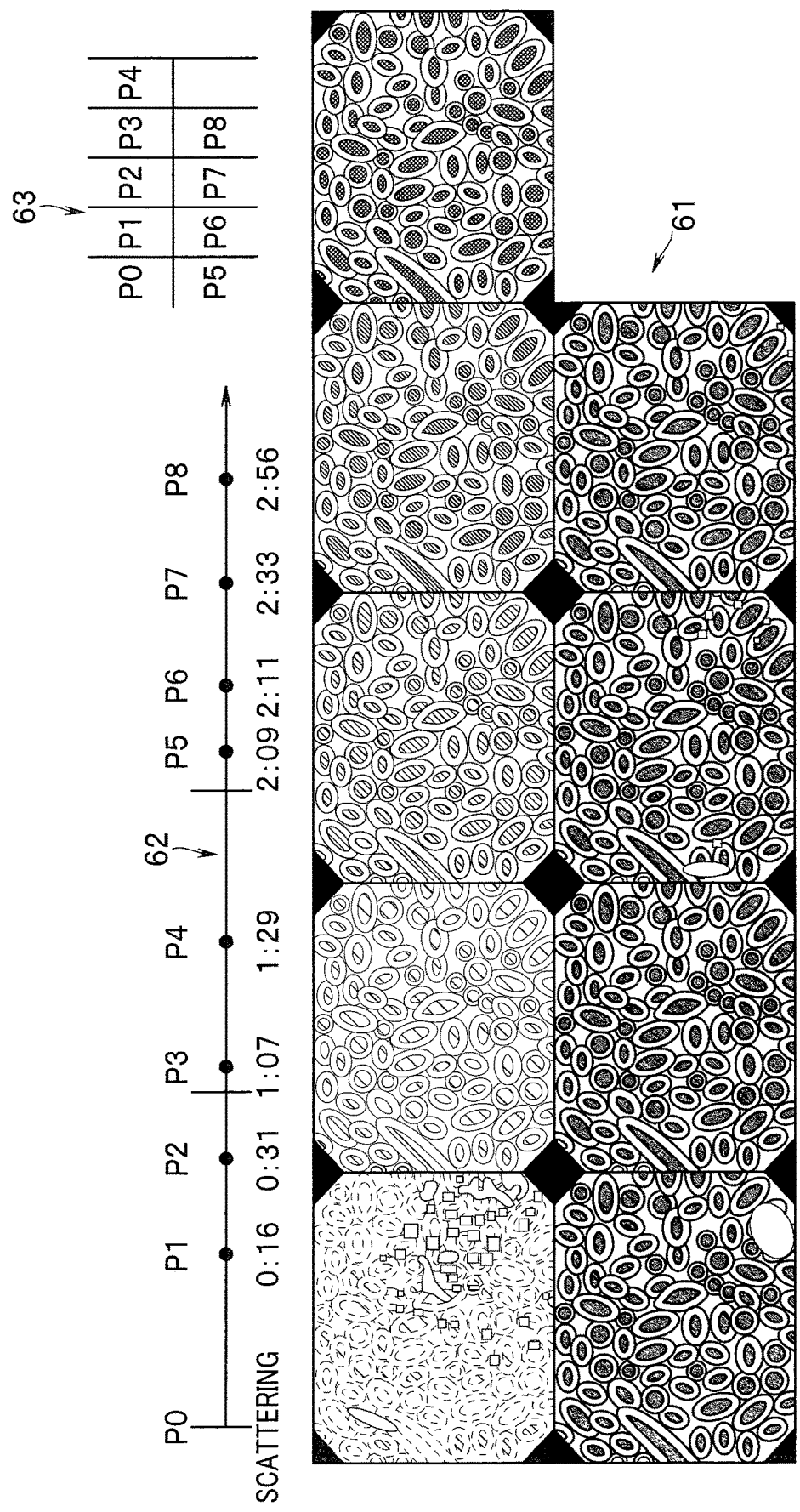
FIG. 10 is a diagram showing a display example of images of the subject sorted in a time-series order, in the image analysis system according to the first embodiment.

FIG. 10 is a diagram showing a display example of subject images that are sorted in a time-series order in the image analysis system according to the first embodiment.

Note that the display example in FIG. 10 shows a state where the image arrangement display 61, the image acquisition time display 62, and the image arrangement order display 63 are displayed on the display apparatus 5.

In the image arrangement display 61, subject images P0 to P8 acquired through the endoscope 2 are displayed in the acquisition time order.

In the image acquisition time display 62, respective time points at which the images P1 to P8 have been acquired after impartment of the load (scattering of glucose in the present embodiment) are shown along a time axis with arrangement of acquisition times, for example.

Note that the image P0 is acquired before scattering of glucose (for example, immediately before scattering of glucose), but is displayed at the position of scattering of glucose for convenience in the example shown in FIG. 10 (of course, the time axis may be extended to a time point before scattering of glucose such that the acquisition time point of the image P0 is correctly shown).

The image arrangement order display 63 displays association of the respective images displayed in the image arrangement display 61 with the images P0 to P8 shown in the image acquisition time display 62, in terms of the respective acquisition time points.

Referring back to FIG. 5, next, the image analysis apparatus (the video processor 3) determines whether or not any image that has not undergone a process, which is described later with reference to steps S12 to S19, exists (step S11).

When an unprocessed image is determined to exist, image data to be processed is inputted from the image input unit 32 to the region extraction unit 33 (step S12).

Next, a region IR of an inappropriate element (an inappropriate region) (see FIGS. 11, 13, etc.) such as a halation region, etc. which is not appropriate for extraction of color component values is excluded from process targets (step S13). Examples of the inappropriate region IR include a region where air bubbles have occurred and an out-of-focus region, in addition to a region where halation has occurred.

Moreover, an average luminance is calculated for each predetermined-sized partial region in the image and the region the average luminance of which is equal to or higher than a predetermined value is selected as an appropriate luminance region (step S14).

Figure 11:
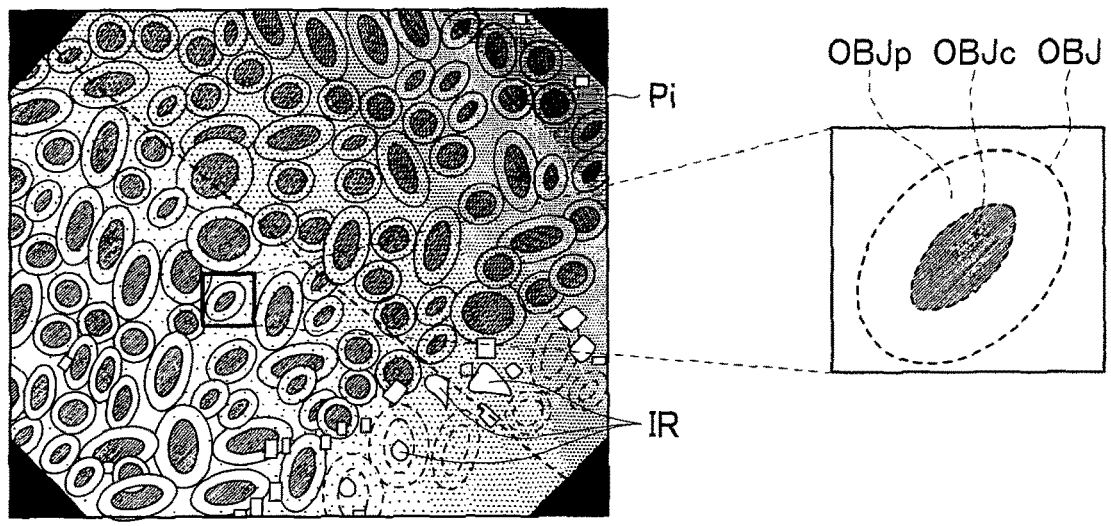
FIG. 11 is a diagram showing a brightness distribution of an image of the subject in the image analysis system according to the first embodiment, with an enlarged view of one element of interest.

For example, in an image Pi (wherein i represents any one of 0 to 8 (that is, Pi is any of P0 to P8) in the example shown in FIG. 10) shown in FIG. 11 (or FIG. 13), the average luminance of the upper right half region is lower than the predetermined value. FIG. 11 is a diagram showing the brightness distribution of a subject image, with an enlarged view showing one element of interest.

In the above description, the analysis target regions are determined by use of, as images for showing the performance of the image pickup apparatus which acquires images inputted through the image input unit 32, subject images acquired by the endoscope 2, etc. However, the present embodiment is not limited to such a method. A method of setting, as the analysis target regions, regions AR (see FIG. 15) appropriate for extraction of color component values, from an average luminance calculated for each predetermined-sized partial region, may be used on the basis of any other images indicating the performance of the image pickup apparatus (for example, an image obtained by photographing an object such as a test plate or a white balance cap which is uniformly colored and is flat, or an image serving as a performance index such as a simulation result SI (see FIG. 14) of the brightness which can be obtained from the design value of the endoscope 2).

Figure 14:
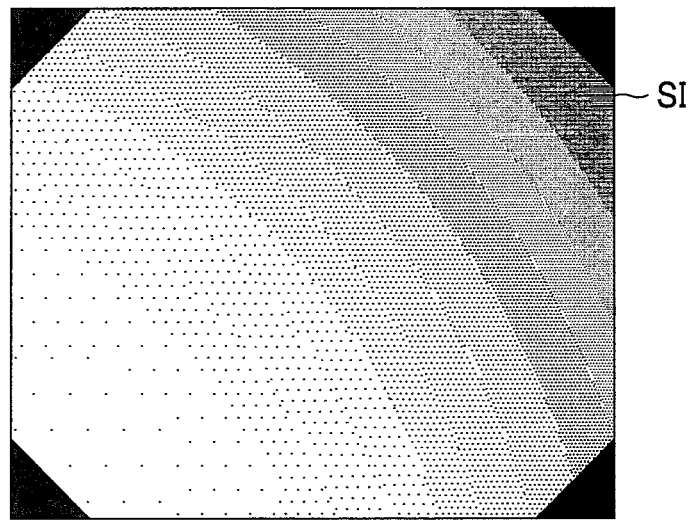
FIG. 14 is a diagram showing one example of a simulation result of endoscope brightness in the image analysis system according to the first embodiment.
Figure 15:
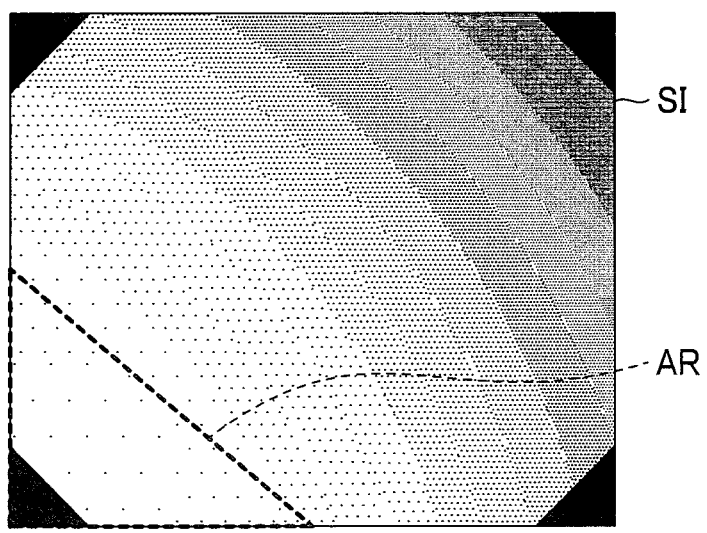
FIG. 15 is a diagram showing one example of a region which is obtained, from the simulation result of the endoscope brightness, as being appropriate for extraction of color component values, in the image analysis system according to the first embodiment.

Alternatively, a method of determining the analysis target regions from among the regions AR appropriate for extraction of the color component values, on the basis of an average luminance calculated for each predetermined-sized partial region, may be used. FIG. 14 is a diagram showing one example of a simulation result of endoscope brightness in the image analysis system according to the first embodiment, or is a diagram showing one example of the simulation result SI of the endoscope 2 brightness. FIG. 15 is a diagram showing one example of a region which is appropriate for extraction of color component values and which is obtained from the simulation result of the endoscope brightness, in the image analysis system according to the first embodiment, and shows one example of the region AR appropriate for extraction of color component values obtained from the simulation result SI of the endoscope 2 brightness.

In the present embodiment, the region extraction unit 33 selects, as an appropriate luminance region, the lower left half region of the image Pi the average luminance of which is equal to or higher than the predetermined value. The selection is performed to select a bright region which is appropriate for extraction of color component values of analysis target regions and to exclude a dark region which is not appropriate for extraction of color component values.

Here, a range the average luminance of which is equal to or higher than the predetermined value is defined as the appropriate luminance range appropriate for extraction of color component values. However, an excessively-bright region the average luminance of which is almost the saturated pixel value may be also excluded. In this case, a range the average luminance of which is equal to or higher than a predetermined lower threshold but equal to or lower than a predetermined upper threshold may be defined as the appropriate luminance range appropriate for extraction of color component values.

Referring back to FIG. 5 again, the region extraction unit 33 subsequently selects center portions OBJc (each of the center portions OBJc is also an element) of multiple elements of interest (intestinal villus image parts, in the present embodiment) OBJ in the selected region (step S15).

Two or more intestinal villus image parts which are the elements of interest OBJ are extracted and selected automatically through execution of image analysis, etc. (however, an option for allowing a user to manually select an element while viewing an image, may be additionally prepared), as described with reference to FIGS. 6 to 9 later.

Each of the intestinal villus image parts which are the element of interest OBJ is an element including an annular surrounding portion OBJp (the shape of which is not limited to an annular shape but may be an arbitrarily defined closed curve shape) and a center portion OBJc surrounded by the surrounding portion OBJp and colored with a color different from the color of the surrounding portion OBJp.

Figure 12:
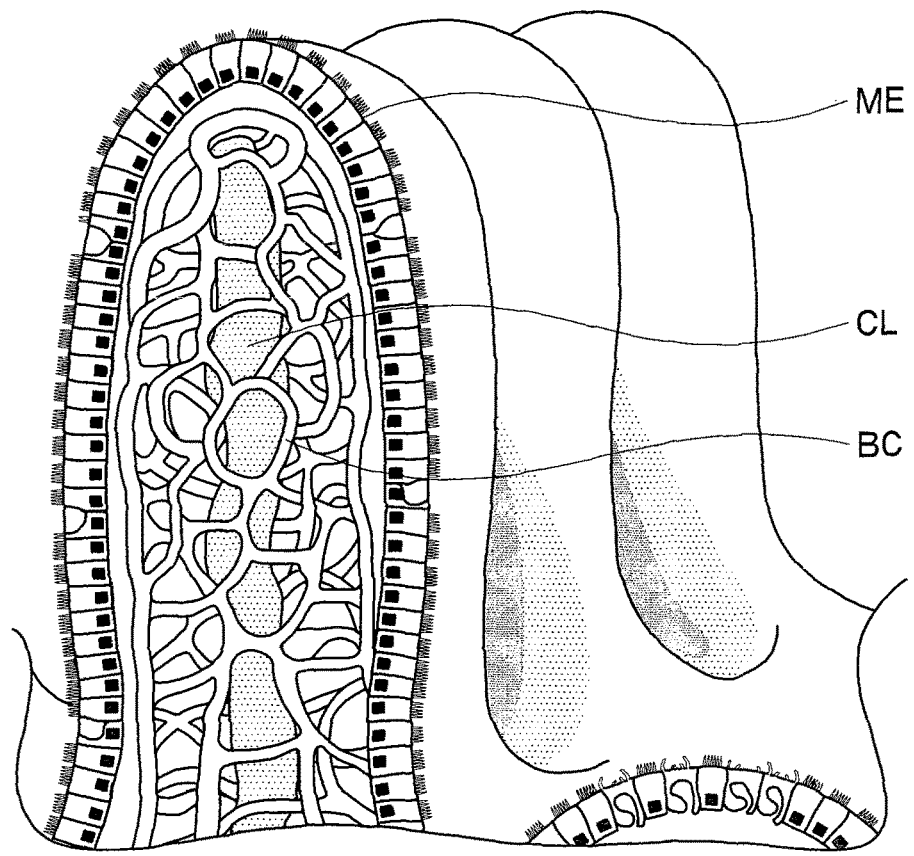
FIG. 12 is a diagram illustrating a structure of an intestinal villus which is an element of interest in the image analysis system according to the first embodiment.

FIG. 12 is a diagram showing the structure of an intestinal villus which is an element of interest in the image analysis system according to the first embodiment.

The intestinal villus has a structure in which capillaries BC are distributed in an area around a center lymph vessel CL which is positioned in the center part and a mucous epithelium ME is formed outside the capillaries BC so as to configure a surface of the villus.

When the intestinal villus is magnified and observed with NBI using light which is narrow-banded to a wavelength so as to be readily absorbable into hemoglobin in blood, the area of the capillaries BC and the area of the mucous epithelium ME are observed in different colors.

When the villus image part obtained by picking up an image of the villus from above, the mucous epithelium ME image part is observed as an annular surrounding portion OBJp, and the capillary BC image part surrounded by the mucous epithelium ME is observed as a center portion OBJc in a color different from the color of the mucous epithelium ME. Therefore, as described later, the color difference between the center portion OBJc and the surrounding portion OBJp is utilized in determination of the element of interest OBJ.

Figure 13:
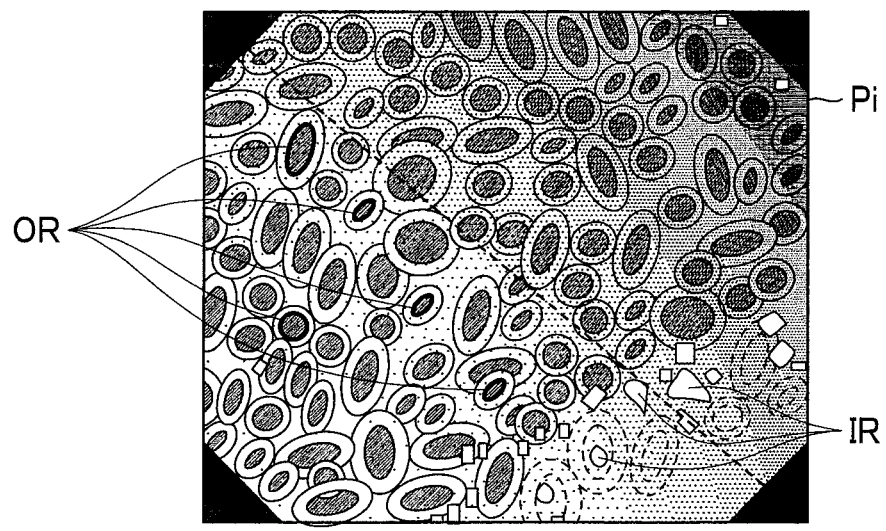
FIG. 13 is a diagram showing an example of an analysis target region set in an image of the subject, in the image analysis system according to the first embodiment.

Referring back to FIG. 5, the region extraction unit 33 further selects, from among the selected plurality of center portions OBJc, a predetermined number (five in the example shown in FIG. 13) of the center portions OBJc that have brightness close to the median, and sets the predetermined number of selected center portions OBJc as the analysis target regions OR (step S16). FIG. 13 is a diagram showing an example of the analysis target regions OR set in the subject image Pi.

The reason why the center portions OBJc that have brightness close to the median are selected at step S16 is that portions having the most appropriate brightness for samples are set as analysis targets. As the brightness, a luminance value calculated on the basis of a plurality of color components may be used. Alternatively, a value obtained by simply adding the plurality of color components may be used as an index of the brightness, or the brightness may be obtained on the basis of the plurality of color components by another method. The analysis target regions OR thus obtained and shown in FIG. 13 include, for example, the center portions OBJc of five intestinal villus image parts.

Next, the color component value extraction unit 36 of the distribution characteristic value calculation unit 34 extracts the color component values, for example, R, G, B component values of each of pixels configuring each analysis target region OR (step S17).

That is, the color component value extraction unit 36 extracts the color component values (R, G, B component values) of each pixel configuring each of the analysis target regions OR in the first image extracted by the region extraction unit 33, and the color component values (R, G, B component values) of each pixel configuring each of the analysis target regions OR in the second image.

Thereafter, the total luminance value calculation unit 37 of the distribution characteristic value calculation unit 34 calculates the total luminance value (the first total luminance value) of the respective color component values concerning the first image extracted by the color component value extraction unit 36, and also calculates the total luminance value (the second total luminance value) of the respective color component values concerning the second image extracted by the color component value extraction unit 36.

Next, the luminance-value distribution characteristic value calculation unit 38 of the distribution characteristic value calculation unit 34 calculates the respective total luminance values calculated by the total luminance value calculation unit 37, that is, respective distribution characteristic values concerning the first total luminance value and the second total luminance value, that is, a first distribution characteristic value and a second distribution characteristic value (step S18).

Note that the "distribution characteristic value" in the present embodiment is obtained as a standard deviation or dispersion, as described above.

Next, the image analysis unit 35 calculates, as the degree of change of the post-load image with respect to the prior-to-load image, the amount of change in the distribution characteristic value which is calculated by the luminance-value distribution characteristic value calculation unit 38 (step S19), as follows, for example.

That is, the image analysis unit 35 calculates, as the amount of change, the absolute value of the difference between the first distribution characteristic value and the second distribution characteristic value by using the following equation 1:

$$\text{amount of change} = <2> - <1> \quad \text{[Equation 1]}$$

wherein <1> represents the first distribution characteristic value concerning the first image (the prior-to-load image) calculated by the luminance-value distribution characteristic value calculation unit 38 and <2> represents the second distribution characteristic value concerning the second image (the post-load image) calculated by the luminance-value distribution characteristic value calculation unit 38.

Figure 16:
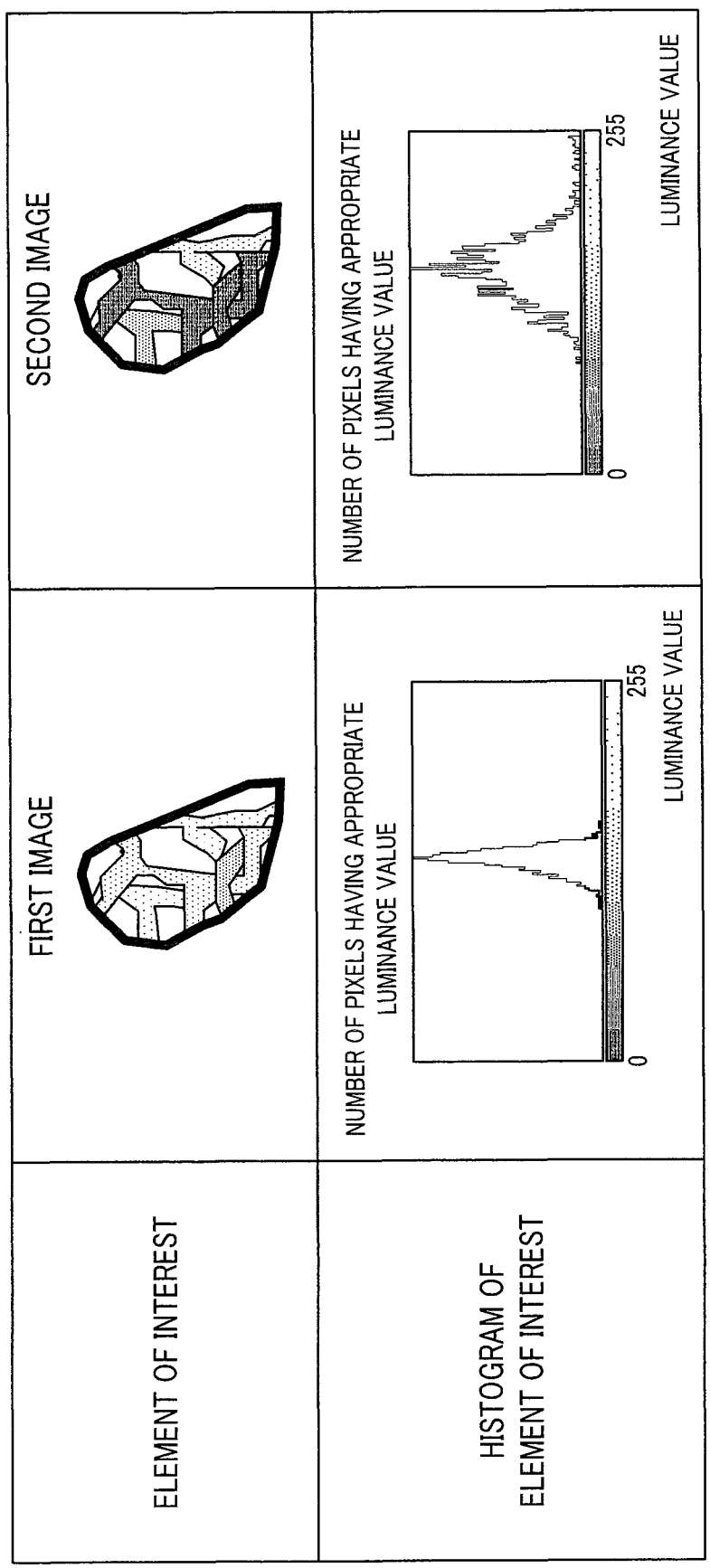
FIG. 16 is a diagram showing change of a distribution characteristic value of luminance values of images before and after impartment of a load to the subject, in the image analysis system according to the first embodiment.

FIG. 16 is a diagram showing change of the distribution characteristic value of the luminance values of images before and after impartment of the load to the subject, in the image analysis system according to the first embodiment.

The upper row in FIG. 16 shows the first image (the prior-to-load image) which is acquired before impartment of the load (the predetermined action) to the subject, that is, before scattering of glucose to an intestine (for example, immediately before scattering of glucose) in the present embodiment, and further shows the second image (the post-load image) which is acquired after impartment of the load (for example, after the elapse of 180 seconds since the scattering).

In the present embodiment, as described above, when glucose as one example of the load (the predetermined action) to the subject, is administered to the subject, observation is time-sequentially continued for approximately three minutes after the impartment of the load (after the predetermined action). Therefore, an image acquired after the elapse of 180 seconds since scattering, for example, is used as the second image which is a post-load image.

In the first image and the second image, elements of interest to be extracted as analysis target regions are surrounded by respective thick lines.

Furthermore, the lower row in FIG. 16 shows histograms in which the respective horizontal axes indicate the luminance values of analysis target regions in the first image and the second image and the respective vertical axes indicate the number of pixels corresponding to the appropriate luminance value.

In the example shown in FIG. 16, when both the images (the first image and the second image) are viewed with naked eyes, the color contrast of the inside of the analysis region is small in the first image acquired before scattering of glucose, whereas the color contrast in a villus included in the analysis region is large in the second image acquired after scattering of the medicinal solution because the blood flow in the villus is increased due to the scattering.

Regarding a standard deviation which is the distribution characteristic value calculated by the distribution characteristic value calculation unit 34 (the color component value extraction unit 36, the total luminance value calculation unit 37, and the luminance-value distribution characteristic value calculation unit 38) and the image analysis unit 35 of the present embodiment, the example in FIG. 16 shows that, as a result, the standard deviation of the luminance values in the villus becomes larger in the second image acquired after scattering of glucose than in the first image acquired before the scattering.

Accordingly, the image analysis system of the present embodiment provides an effect that can realize image quantification of an endoscope image which agrees with viewing by naked eyes.

That is, when capillaries and other tissues which are generally included in a villus are evaluated using an average value, the degree of color change of a vessel network in the villus may become less conspicuous, but the image analysis system of the present embodiment focuses on the luminance distribution in a villus, whereby the color change of a vessel network can be extracted. Furthermore, the contrast to other tissues can be made clear. Accordingly, not only the change of a blood flow rate but also the change of a fat absorption amount can be observed.

Next, a subroutine concerning step S15 shown in FIG. 5 is described.

Figure 6:
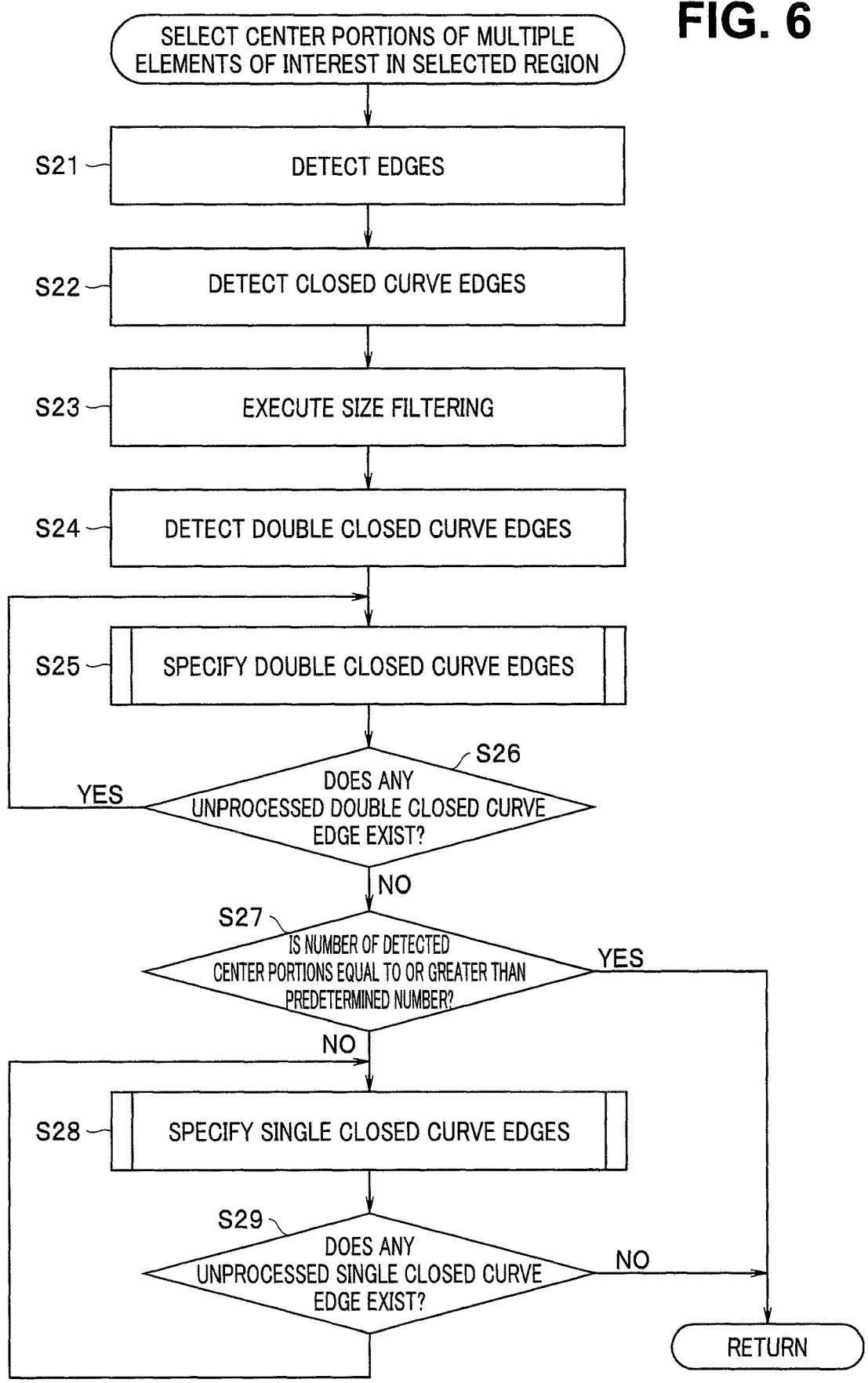
FIG. 6 is a flowchart showing a process of selecting the center portions of multiple elements of interest in a selected region, in the image analysis apparatus in the image analysis system according to the first embodiment.

FIG. 6 is a flowchart showing a process of selecting the center portions of multiple elements of interest in the selected region, in the aforementioned image analysis apparatus (the video processor 3).

When the process proceeds to step S15 shown in FIG. 5, the edge detection unit 51 performs edge detection filtering on the selected region (for example, the lower left half region of the image Pi in FIG. 11), and thereby, extracts edge components (step S21).

Next, the closed-curve edge detection unit 52 further detects edges each forming a closed curve, from among the edges detected by the edge detection unit 51 (step S22).

Next, the size filtering unit 53 calculates the sizes (for example, the maximum diameter of the closed curves, the average diameter of the closed curves, the areas of regions surrounded by the closed curves, etc.) of the closed curve edges detected by the closed-curve edge detection unit 52, and selects only a closed curve edge the calculated size of which falls within such a range that can be taken by an element of interest (for example, within such a range that can be taken by an intestinal villus) (step S23).

Next, the double-closed-curve edge detection unit 54 detects all the double closed curve edges from among the closed curve edges filtered by the size filtering unit 53 (step S24).

Note that each of the inner closed curve edge and the outer closed curve edge configuring each double closed curve edge has undergone the process performed at step S23 by the size filtering unit 53, and thus, is a closed curve edge that has been determined to have a size falling within such a range that can be taken by an element of interest.

Further, the double-closed-curve edge specification unit 55 specifies whether or not each of the double closed curve edges detected by the double-closed-curve edge detection unit 54 falls under an element of interest (step S25). Note that a subroutine concerning step S25 is described later (see FIG. 8).

Subsequently, the region extraction control unit 57 determines whether or not any double closed curve edge having not undergone step S25 exists among the double closed curve edges detected by the double-closed-curve edge detection unit 54 (step S26). When such a double closed curve edge exists, step S25 is executed on the next double closed curve edge.

When all the double closed curve edges are thus determined, at step S26, to have undergone step S25, the region extraction control unit 57 determines whether or not the number of double closed curve edges that have been determined as elements of interest (i.e., the number of the center portions of the detected elements of interest) is equal to or greater than a predetermined number (five in the example shown in FIG. 13) (step S27).

When the number of double closed curve edges that have been determined to fall under elements of interest is determined to be less than the predetermined number, the single-closed-curve edge specification unit 56 specifies whether or not a single closed curve edge (which has undergone step S23 by the size filtering unit 53, and has been determined to have such a size as to fall within a range that can be taken by an element of interest) determined to be not a double closed curve edge, falls under an element of interest (step S28). Note that a subroutine concerning step S28 is described later (see FIG. 9).

Next, the region extraction control unit 57 determines whether or not any single closed curve edge that has not undergone step S25 exists among the single closed curve edges (step S29). When such a single closed curve edge exists, step S28 is executed on the next single closed curve edge.

Accordingly, when all the single closed curve edges are determined, at step S29, to have undergone step S28, or when the number of double closed curve edges that have been determined, at step S27, to fall under elements of interest is equal to or greater than the predetermined number, the process returns to the process shown in FIG. 5.

In this way, double closed curve edges that are more likely to fall under elements of interest are specified first, and then, whether or not single closed curve edges fall under elements of interest are further specified if the number of double closed curve edges determined to fall under elements of interest is less than the predetermined number.

In the process in FIG. 6, when the number of double closed curve edges reaches the predetermined number, specification of single closed curve edges is not executed. However, specification of single closed curve edges may be executed irrespective of whether or not the number of double closed curve edges reaches the predetermined number.

Figure 7:
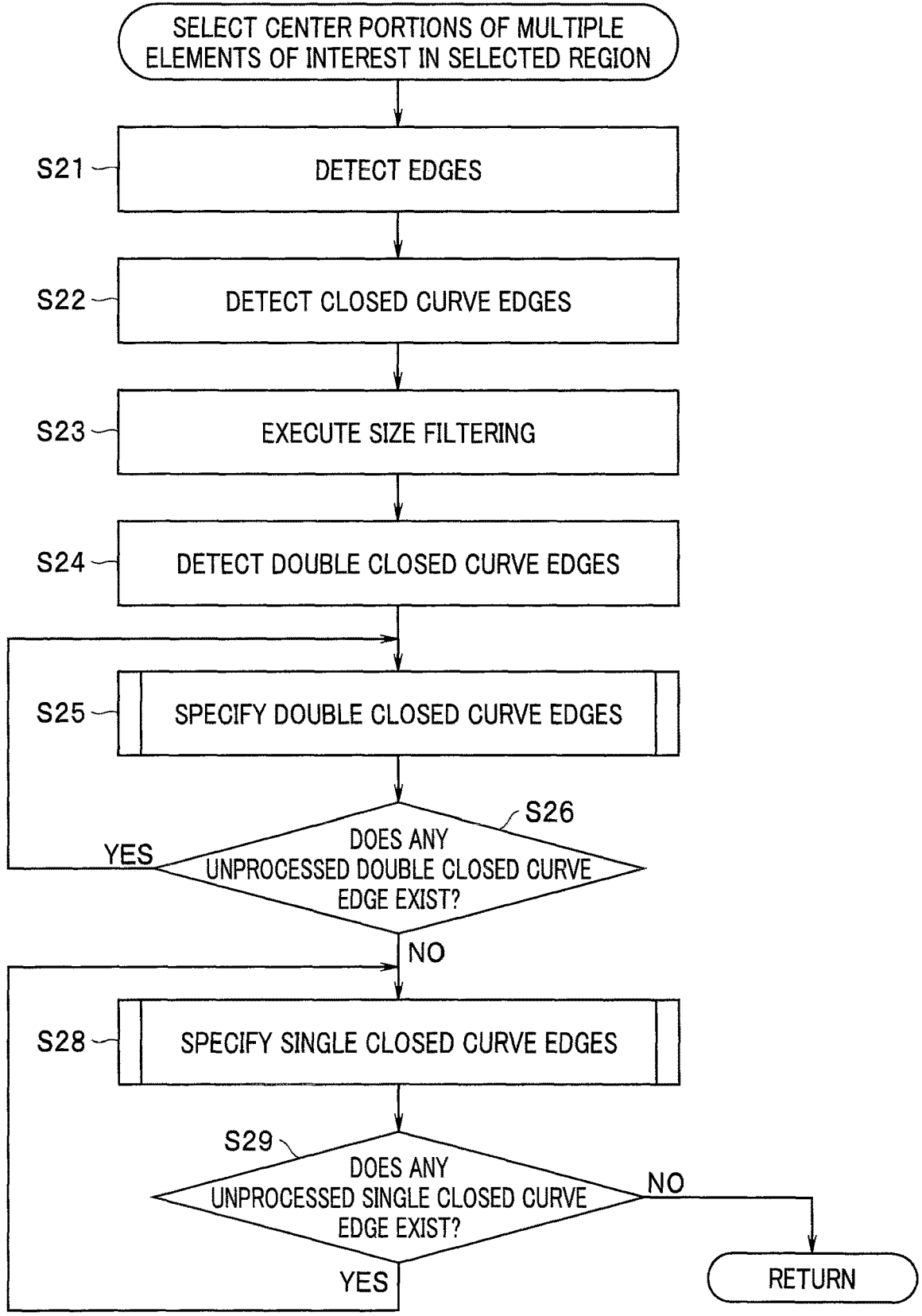
FIG. 7 is a flowchart showing a modification of the process of selecting the center portions of multiple elements of interest in a selected region, in the image analysis apparatus in the image analysis system according to the first embodiment.

FIG. 7 is a flowchart showing a modification of a process of selecting the center portions of multiple elements of interest in the selected region, in the image analysis apparatus (the video processor 3).

The process shown in FIG. 7 is obtained by omitting step S27 in FIG. 6. Through the process, not only double closed curve edges but also single closed curve edges are specified so that the center portions of more elements of interest can be selected.

Figure 8:
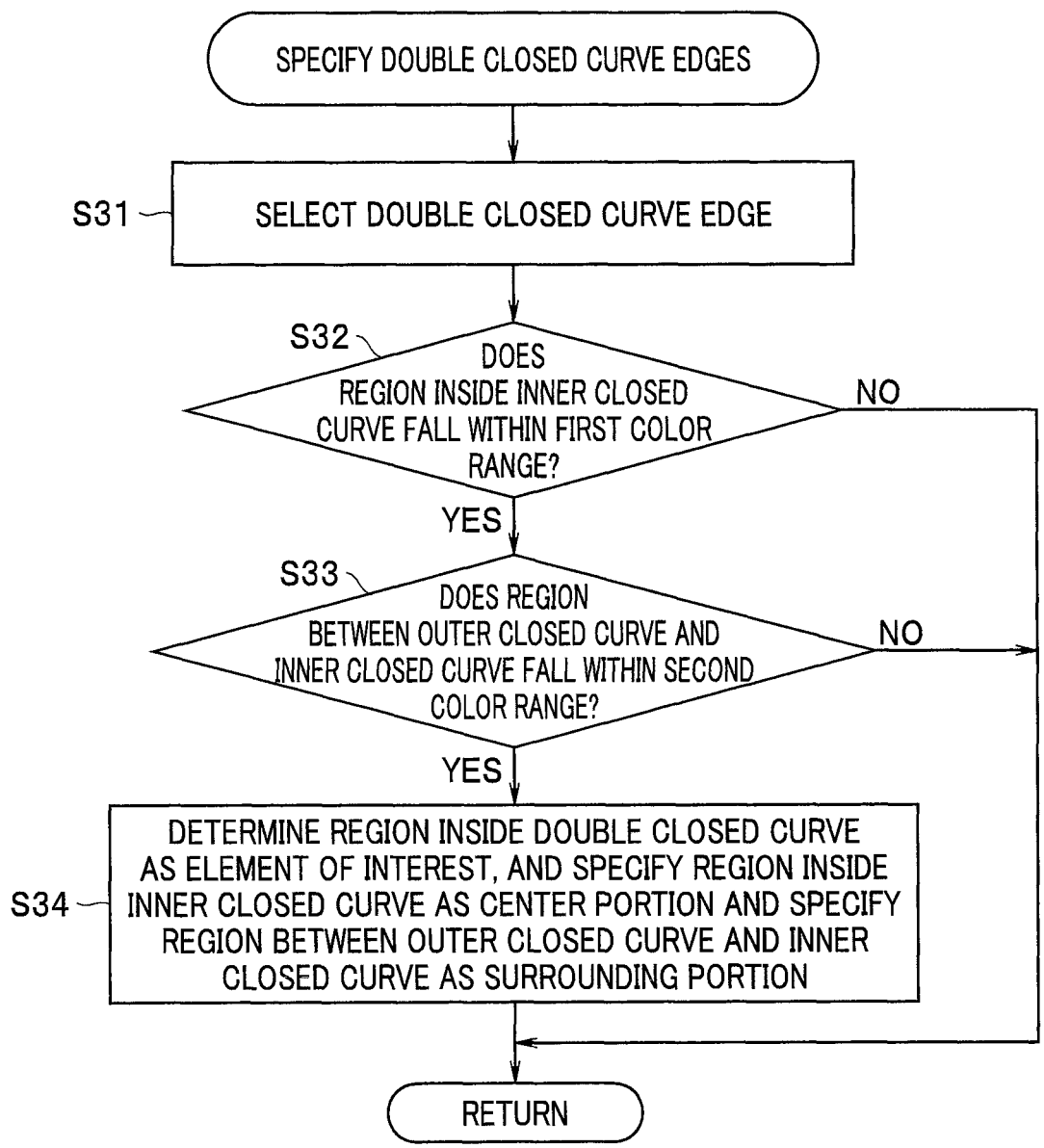
FIG. 8 is a flowchart showing a double closed curve edge specification process in the image analysis apparatus in the image analysis system according to the first embodiment.

FIG. 8 is a flowchart showing a double-closed-curve edge specification process as a subroutine concerning step S25 in FIG. 6 (or FIG. 7) in the image analysis apparatus.

When the process proceeds to step S25 (specification of double closed curve edges) in FIG. 6 (or FIG. 7), the double-closed-curve edge specification unit 55 selects, from among double closed curve edges detected by the double-closed-curve edge detection unit 54 at step S24 (see FIG. 6), one unprocessed double closed curve edge (step S31).

Next, the double-closed-curve edge specification unit 55 determines whether or not, for example, the average value of the color component values of each of pixels inside the inner closed curve edge of the selected double curve edge falls within the first color range corresponding to the center portion of an element of interest (step S32).

When the average value is determined to fall outside the first color range, the double closed curve edge selected at step S31 is not identified as an element of interest and the process returns to the process shown in FIG. 6 (or FIG. 7, the same applies hereinafter).

Alternatively, when the average value is determined to fall within the first color range at step S32, the double-closed-curve edge specification unit 55 further determines whether or not, for example, the average value of the color component values of each of pixels between the outer closed curve edge and the inner closed curve edge of the selected double closed curve edge falls within the second color range corresponding to the surrounding portion of an element of interest (step S33).

When the average value is determined to fall outside the second color range, the double closed curve edge selected at step S31 is not identified as an element of interest and the process returns to the process shown in FIG. 6.

When the average value is determined to fall within the second color range at step S33 (that is, when the color of the region inside the inner closed curve edge and the color of the region between the inner closed curve edge and the outer closed curve edge are determined to differ from each other), the double closed curve edge selected at step S31 is determined to fall under an element of interest, and the region inside the inner closed curve edge and the region between the outer closed curve edge and the inner closed curve edge are specified as the center portion of the element of interest and the surrounding portion of the element of interest, respectively (step S34). Thereafter, the process returns to the process shown in FIG. 6.

Figure 9:
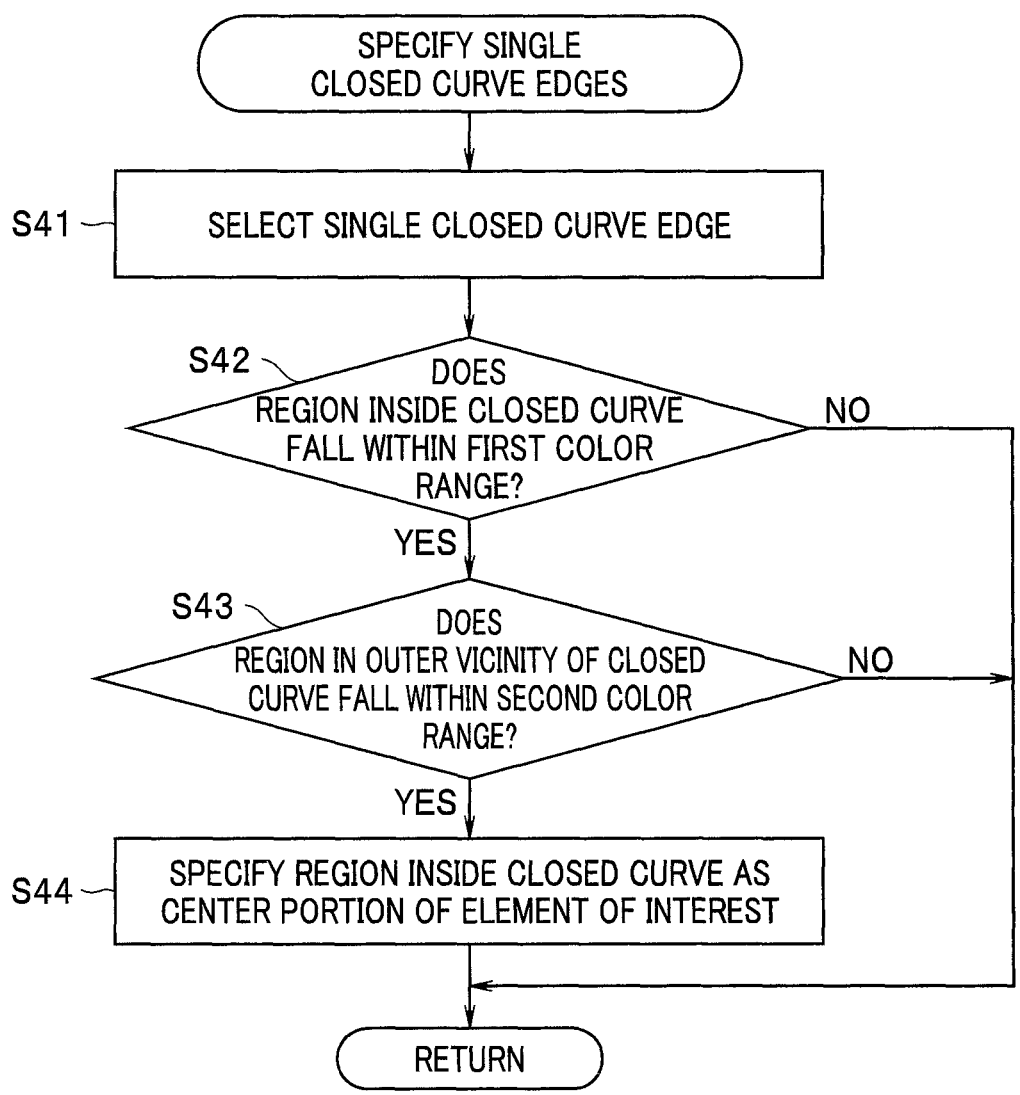
FIG. 9 is a flowchart showing a single closed curve edge specification process in the image analysis apparatus in the image analysis system according to the first embodiment.

FIG. 9 is a flowchart showing a single closed curve edge specification process, as a subroutine concerning step S28 in FIG. 6 (or FIG. 7), in the image analysis apparatus.

When the process proceeds to step S28 (the single closed curve edge specification process) in FIG. 6 (or FIG. 7), the single-closed-curve edge specification unit 56 selects, from among closed curve edges filtered by the size filtering unit 53, unprocessed one of single closed curve edges other than double closed curve edges (step S41).

Next, the single-closed-curve edge specification unit 56 determines whether or not, for example, the average value of the color component values of each of pixels inside the selected single closed curve edge falls within the first color range corresponding to the center portion of an element of interest (step S42).

When the average value is determined to fall outside the first color range, the single closed curve edge selected at step S41 is not identified as an element of interest and the process returns to the process shown in FIG. 6.

When the average value is determined to fall within the first color range at step S42, the single-closed-curve edge specification unit 56 further determines whether or not, for example, the average value of the color component values of each of pixels in the outer vicinity of the selected single closed curve edge falls within the second color range (a color range different from the first color range) corresponding to the surrounding portion of an element of interest (step S43).

When the average value is determined to fall outside the second color range, the single closed curve edge selected at step S41 is not identified as an element of interest and the process returns to the process shown in FIG. 6.

When the average value is determined to fall within the second color range at step S43 (that is, when the color of the region inside the single closed curve edge and the color of the region in the outer vicinity of the single closed curve edge are determined to differ from each other), the region inside the single closed curve edge selected at step S41 is specified as the center portion of an element of interest (step S44). Thereafter, the process returns to the process shown in FIG. 6.

In FIGS. 6 to 9 described above, various processes including edge detection (closed curve edge detection, double-closed-curve edge detection), size filtering, and color range determination are carried out to increase the accuracy of detecting elements of interest. However, any of the processes may be omitted to reduce the process load such that the detection speed is increased.

As described above, according to the first embodiment, the region extraction unit 33 specifies an element of interest including an annular surrounding portion and a center portion surrounded by the surrounding portion and colored in a color different from the color of the surrounding portion, and extracts, as an analysis target region, only the center portion of the element of interest, and further, the distribution characteristic value calculation unit 34 and the image analysis unit 35 calculate the degree of change in a luminance value distribution characteristic value (a standard deviation or dispersion) in terms of the color component values in the analysis target region. Accordingly, regardless of the influence of change in the hue, the change of the subject can be accurately analyzed from the time-sequentially acquired subject images.

In addition, since, when the analysis target regions are extracted, an inappropriate element not appropriate for extraction of color component values is excluded, a more accurate image analysis result can be obtained regardless of the inappropriate element.

Further, since the center portions of the predetermined number of elements of interest that have brightness closed to the median are extracted as the analysis target regions, the amount of change can be more appropriately discerned.

The image analysis apparatus (or the image analysis system, the same applies hereinafter) has been mainly described above. However, the first embodiment may be an operation method for operating the image analysis apparatus in the aforementioned manner, a processing program for causing a computer to execute the same process as the process to be executed by the image analysis apparatus, a non-temporal recording medium readable by a computer having the process program recorded in the medium, or the like.

<Second Embodiment>

Next, a second embodiment of the present invention is described.

An endoscope system (an image analysis system) according to the second embodiment has basic components identical to the components of the first embodiment. Thus, only the difference from the first embodiment is described and a description of other details is omitted.

Figure 17:
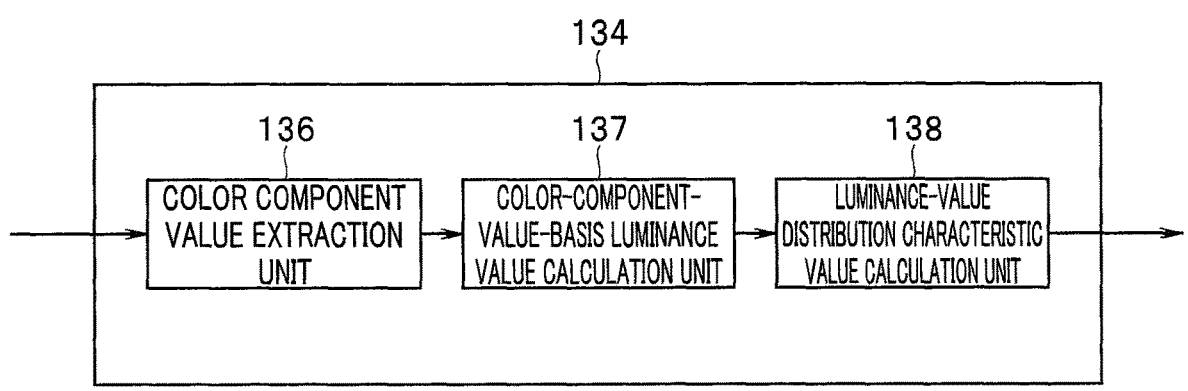
FIG. 17 is a block diagram illustrating a configuration of a distribution characteristic value calculation unit in an image analysis system according to a second embodiment of the present invention.
Figure 18:
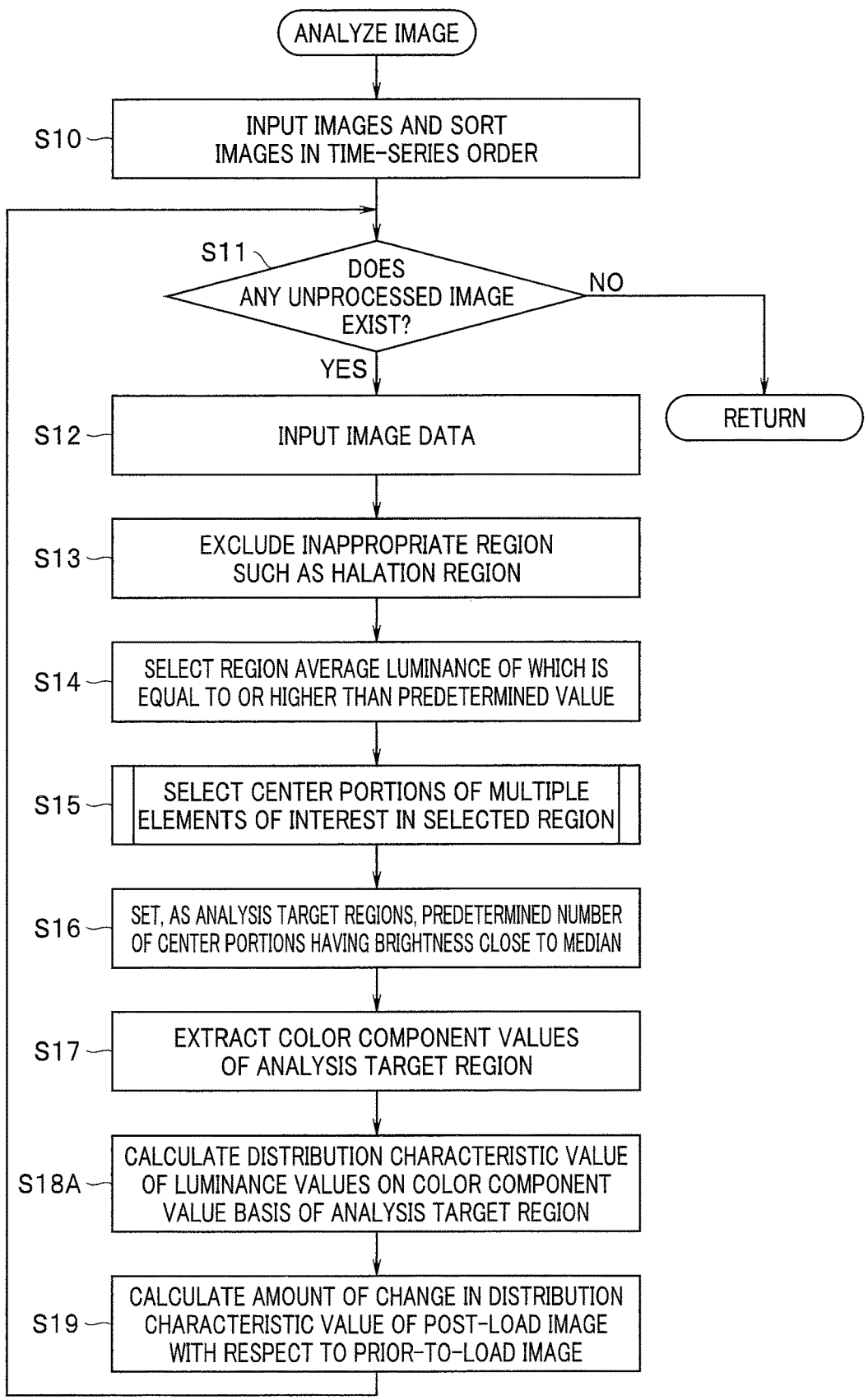
FIG. 18 is a flowchart showing an image analysis process to be executed by an image analysis apparatus in the image analysis system according to the second embodiment.
Figure 19A:
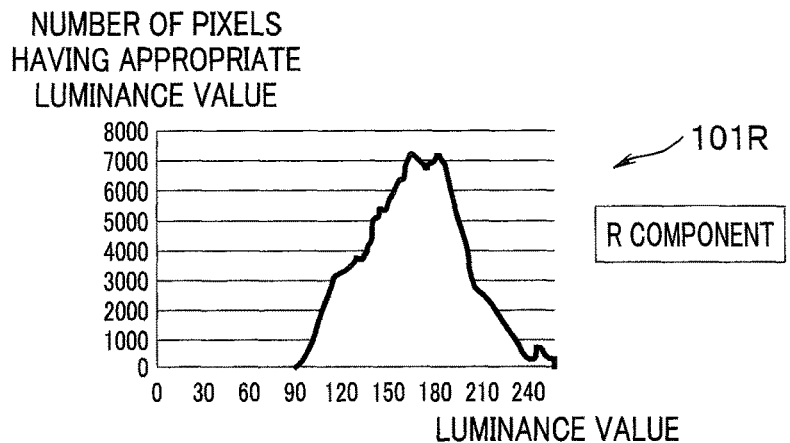
FIG. 19A is a diagram showing one example of a luminance value distribution characteristic of an R component in the image analysis apparatus in the image analysis system according to the second embodiment.
Figure 19B:
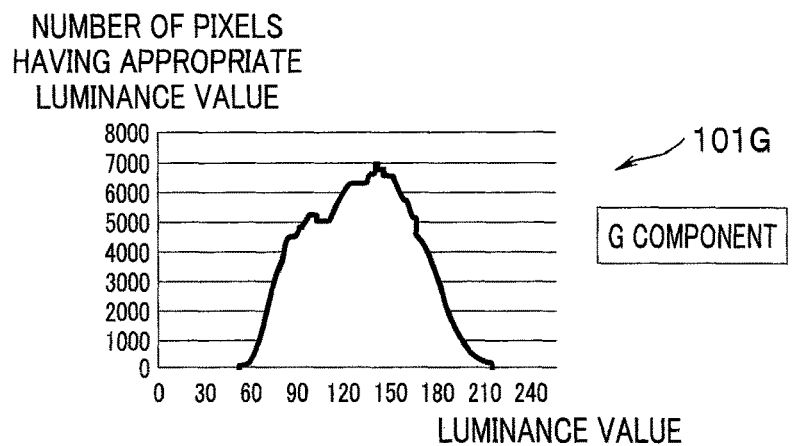
FIG. 19B is a diagram showing one example of a luminance value distribution characteristic of a G component in the image analysis apparatus in the image analysis system according to the second embodiment.
Figure 19C:
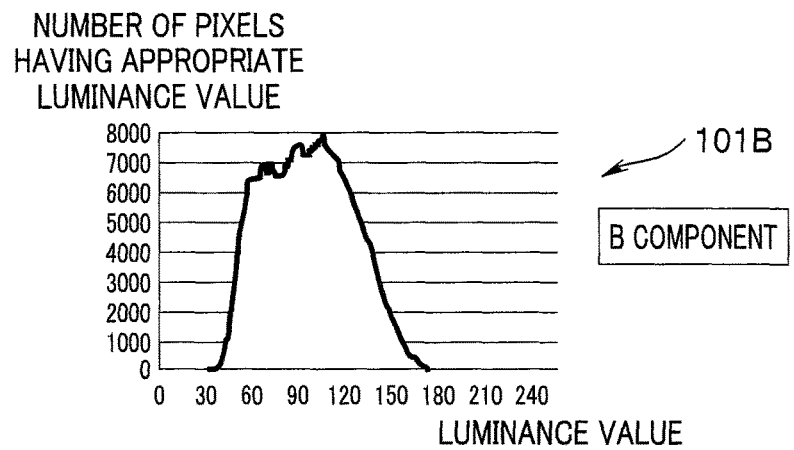
FIG. 19C is a diagram showing one example of a luminance value distribution characteristic of a B component in the image analysis apparatus in the image analysis system according to the second embodiment.

FIG. 17 is a block diagram illustrating the configuration of a distribution characteristic value calculation unit in the image analysis system according to the second embodiment of the present invention. FIG. 18 is a flowchart showing an image analysis process to be executed by an image analysis apparatus in the image analysis system according to the second embodiment of the present invention. FIGS. 19A, 19B, and 19C each show one example of a luminance value distribution characteristic of each color component in the image analysis apparatus in the image analysis system according to the second embodiment.

The endoscope system (the image analysis system) of the first embodiment obtains, on the basis of the color component values (R, G, B component values) acquired by the color component value extraction unit 36 of the distribution characteristic value calculation unit 34, a distribution characteristic value of the total luminance values calculated by the total luminance value calculation unit 37 and the luminance-value distribution characteristic value calculation unit 38.

In contrast, in the endoscope system (the image analysis system) of the second embodiment, the distribution characteristic value calculation unit 134 includes a color component value extraction unit 136, a color-component-value-basis luminance value calculation unit 137, and a luminance-value distribution characteristic value calculation unit 138, as illustrated in FIG. 17.

The color component value extraction unit 136 extracts the respective color component values (R, G, B component values) of each analysis target region of the first image extracted by the region extraction unit 33, and extracts the respective color component values (R, G, B component values) of each analysis target region of the second image extracted by the region extraction unit 33, as in the first embodiment.

The second embodiment is different from the first embodiment in that the color-component-value-basis luminance value calculation unit 137 calculates a luminance value on the respective color component value basis of the analysis target region of each of the first image and the second image extracted by the color component value extraction unit 136, and the luminance-value distribution characteristic value calculation unit 138 calculates respective distribution characteristic values concerning the respective color component value-basis luminance values calculated by the color-component-value-basis luminance value calculation unit 137.

That is, in observation with NBI used in the endoscope system 1 of the second embodiment, normally, blue and green narrow-banded lights are cast onto an intestinal mucous surface, and the blue reflection light is converted to blue and green lights and the green reflection light is converted to a red light, so as to be outputted on a monitor.

Here, when the green and blue reflection lights are compared with each other, capillaries or a fine pattern in a mucous surface layer are more highlighted by the blue light. That is, an analysis result of more accurately showing the capillaries or the fine pattern can be obtained by analysis of the green or blue components outputted on the monitor. On the other hand, when a vessel in a deeper part is focused on, a red component is desirably analyzed.

When the technology of the present invention of calculating the degree of change in the distribution characteristic value of luminance values concerning the color component values of an analysis target region, as described above, is applied to an NBI observation system, focusing on the distribution characteristics of the respective color component value-basis luminance values is more desirable in some cases.

In view of the aforementioned circumstance, in the endoscope system (the image analysis system) of the second embodiment, the distribution characteristic value of the luminance values concerning the analysis target region of each of the first image (the prior-to-load image) and the second image (the post-load image) acquired by the color component value extraction unit, is acquired on each color component value (R, G, B component value) basis instead of totalizing.

<Image Analysis in the Second Embodiment>

FIG. 18 is a flowchart showing an image analysis process to be executed by the image analysis apparatus in the image analysis system according to the second embodiment.

As shown in FIG. 18, at step S17 in the second embodiment, the color component value extraction unit 136 of the distribution characteristic value calculation unit 134 extracts the color component values, for example, R, G, B component values of each of pixels configuring the analysis target region OR (step S17).

That is, the color component value extraction unit 136 extracts the respective color component values (R, G, B component values) of each of pixels configuring the analysis target region OR of the first image extracted by the region extraction unit 33, and the respective color component values (R, G, B component values) of each of pixels configuring the analysis target region OR of the second image extracted by the region extraction unit 33.

Thereafter, the color-component-value-basis luminance value calculation unit 137 of the distribution characteristic value calculation unit 134 calculates the respective luminance values (the first luminance values) for the respective color component values of the first image extracted by the color component value extraction unit 136 and the respective luminance values (the second luminance values) for the respective color component values of the second image extracted by the color component value extraction unit 136.

FIGS. 19A, 19B, and 19C each show one example of distribution characteristics of each color component-basis luminance values of an analysis target region, in the image analysis apparatus in the image analysis system according to the second embodiment.

More specifically, FIG. 19A shows a luminance value distribution characteristic 101R of the R component, FIG. 19B shows a luminance value distribution characteristic 101G of the G component, and FIG. 19C shows a luminance value distribution characteristic 101B of the B component. In each of FIGS. 19A to 19C, a horizontal axis indicates the luminance value in terms of the corresponding each color component of the analysis target region while a vertical axis shows a pixel value corresponding to the luminance value, respectively.

Next, the luminance-value distribution characteristic value calculation unit 138 of the distribution characteristic value calculation unit 134 calculates, for each of the analysis target region of the first image and the analysis target region of the second image, a distribution characteristic value of the respective color component value-basis luminance values calculated by the color-component-value-basis luminance value calculation unit 137 (step S18A).

Next, for each color component value, the image analysis unit 35 of the second embodiment calculates, as the degree of change of the post-load image with respect to the prior-to-load image, the amount of change in each color component value-basis distribution characteristic value calculated by the luminance-value distribution characteristic value calculation unit 138 (step S19).

As described above, the second embodiment provides an effect the same as the effect provided by the first embodiment, and also calculates each color component-basis distribution characteristic values, whereby analysis results specialized in respective feature values can be provided. Accordingly, the second embodiment is particularly effective for observation with NBI.

<Third Embodiment>

Next, a third embodiment of the present invention is described.

An endoscope system (an image analysis system) according to the third embodiment has basic components identical to the components of the first and second embodiments. Thus, only the difference from the first embodiment is described and a description of other details is omitted.

The endoscope systems (the image analysis systems) of the first and second embodiments can support observation with so-called NBI (narrow band imaging), and each of them acquires the aforementioned first image (the prior-to-load image) and the aforementioned second image (the post-load image) through observation with NBI.

In contrast, the endoscope system (the image analysis system) of the third embodiment acquires the aforementioned first image (the prior-to-load image) and the aforementioned second image (the post-load image) through observation using white light.

More specifically, the third embodiment is different from the first embodiment in the filtering performance of the rotary filter 43 of the light source apparatus 4 and the like, but is the same as the first embodiment in terms of the other component and effects.

As described above, the third embodiment provides an effect the same as the effects of the first and second embodiments in which, regardless of the influence of change in the hue, the change of a subject can be accurately analyzed from time-sequentially acquired subject images.

<Fourth Embodiment>

Next, a fourth embodiment of the present invention is described.

An endoscope system (an image analysis system) according to the fourth embodiment has basic components identical to the components of the first to third embodiments, except for the component of a light source apparatus. Thus, only the difference from the first embodiment is described and a description of other details is omitted.

Figure 20:
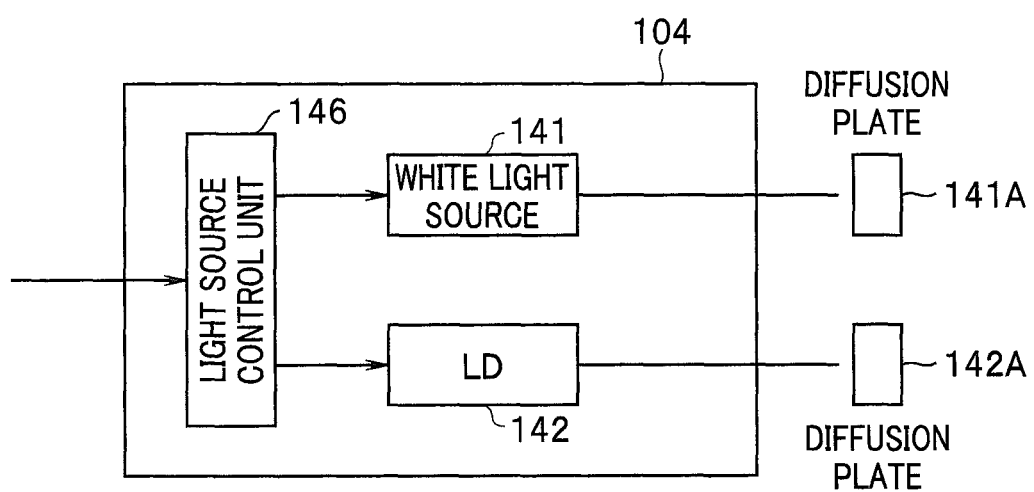
FIG. 20 is a block diagram illustrating a schematic configuration of a light source apparatus in an image analysis system according to a fourth embodiment of the present invention.

FIG. 20 is a block diagram illustrating the schematic configuration of a light source apparatus in the image analysis system according to the fourth embodiment of the present invention.

In each of the endoscope systems (the image analysis systems) of the aforementioned first to third embodiments, the light source apparatus 4 uses a normal light source such as a white light source. In particular, the systems of the first and second embodiments can support observation with so-called NBI (narrow band imaging). In these systems, the aforementioned first image (the prior-to-load image) and the aforementioned second image (the post-load image) are acquired through observation with NBI.

In contrast, the endoscope system (the image analysis system) of the fourth embodiment includes a light source apparatus 104 in place of the light source apparatus 4 of the first embodiment. That is, the endoscope system (the image analysis system) of the fourth embodiment includes a laser light source 142 while including a white light source 141.

More specifically, the light source apparatus 104 of the fourth embodiment includes the white light source 141, the laser light source 142, a light source control unit 146, a diffusion plate 141A, and a diffusion plate 142A.

The white light source 141 is configured by use of a white LED, a xenon lamp, or the like, and generates white light under control by the light source control unit 146.

Light from the white light source 141 is emitted from a fiber bundle composed of multiple optical fibers, and is caused to exit from the illumination unit of the endoscope 2 through the diffusion plate 141A. Note that the fourth embodiment uses a simultaneous-type observation method.

The laser light source 144 is configured by a semiconductor laser light source, and is driven under control by the light source control unit 146. Moreover, light from the laser light source 144 is guided by one optical fiber, and is caused to exist through the diffusion plate 142A.

The other components in the endoscope system, the components of the endoscope 2, and the components of the video processor 3 as the image analysis apparatus are identical to the components in the first embodiment, except for a part according to the simultaneous type observation method. Therefore, a detailed description of the components is omitted.

As described above, the fourth embodiment provides an effect the same as the effect provided by the first embodiment, irrespective of the type of the light source.

<Fifth Embodiment>

Next, a fifth embodiment of the present invention is described.

An endoscope system (an image analysis system) according to the fifth embodiment has basic components identical to the components of the first embodiment. Thus, only the difference from the first embodiment is described and a description of other details is omitted.

Figure 21:
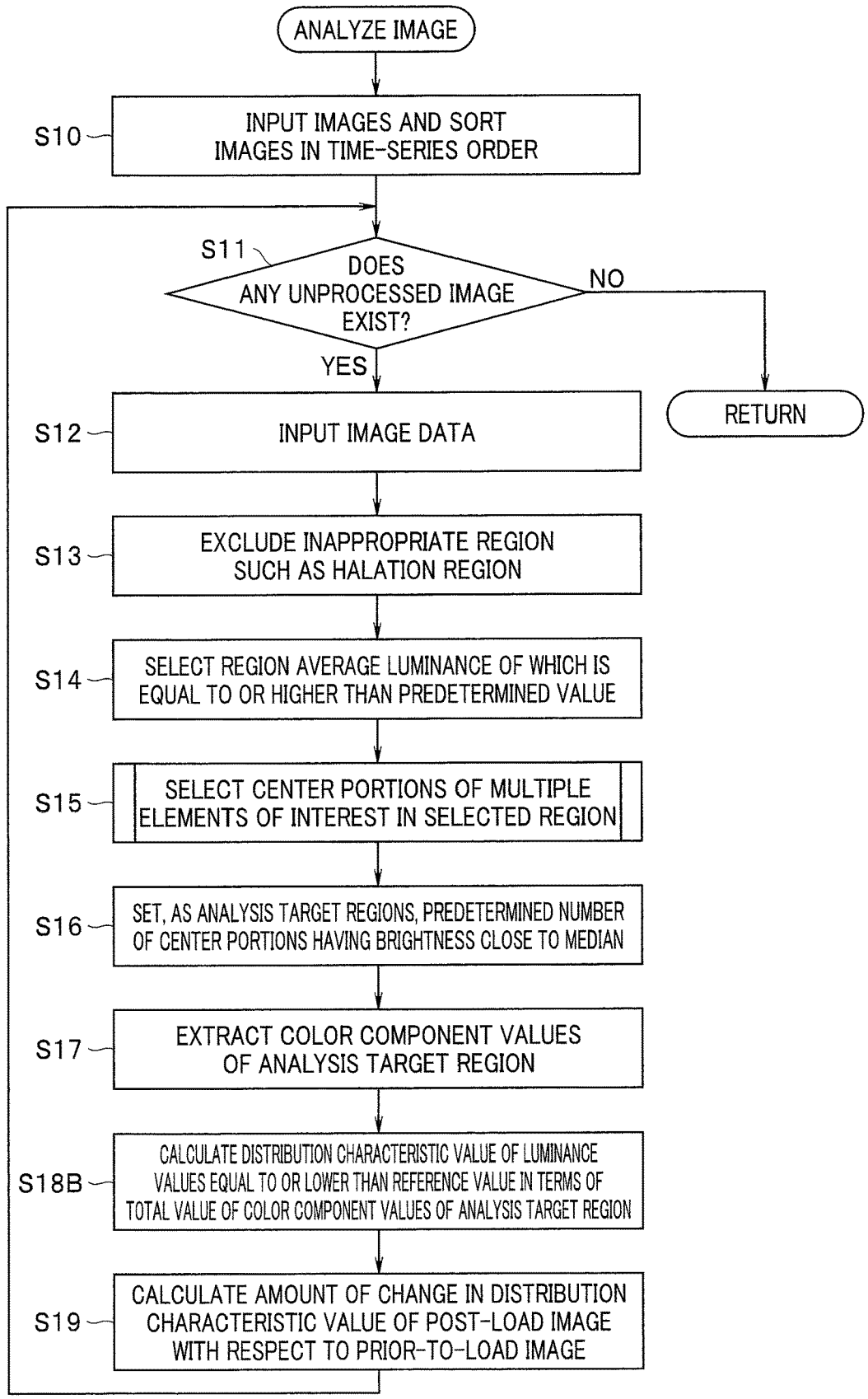
FIG. 21 is a flowchart showing an image analysis process to be executed by an image analysis apparatus in an image analysis system according to a fifth embodiment of the present invention.
Figure 22:
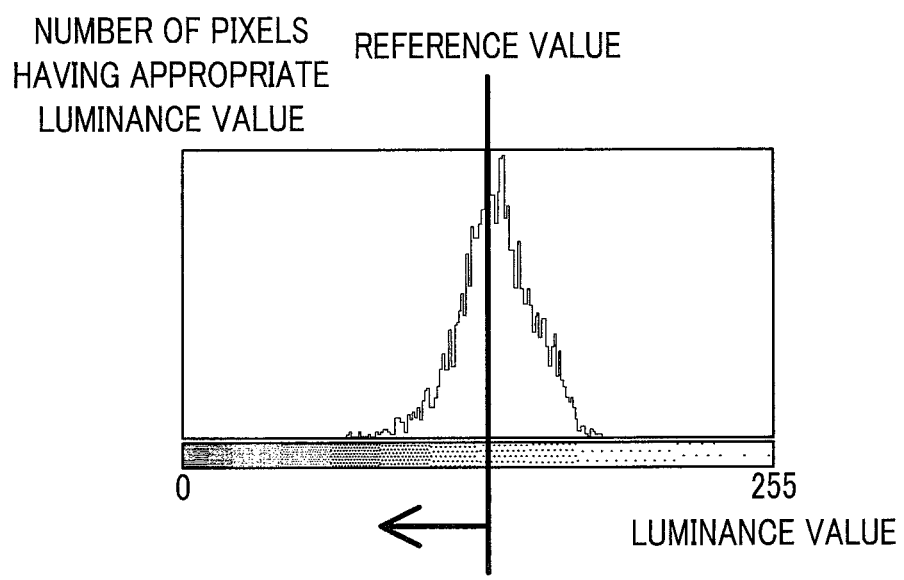
FIG. 22 is a diagram showing that a distribution characteristic value of luminance values equal to or lower than a reference value is calculated in the image analysis apparatus in the image analysis system according to the fifth embodiment.

FIG. 21 is a flowchart showing an image analysis process to be executed by the image analysis apparatus in the image analysis system according to the fifth embodiment of the present invention. FIG. 22 is a diagram showing extraction of distribution characteristic values of luminance values equal to or lower than the reference value in the image analysis apparatus of the image analysis system according to the fifth embodiment.

In the endoscope system (the image analysis system) of the first embodiment, the distribution characteristic value of the luminance values which are totalized by the total luminance value calculation unit 37 and the luminance-value distribution characteristic value calculation unit 38 are obtained on the basis of the respective color component values (R, G, B component values) acquired by the color component value extraction unit 36 of the distribution characteristic value calculation unit 34, and, in terms of the data of all the distribution characteristic values obtained by the image analysis unit 35, the degree of change in each distribution characteristic value is calculated.

In contrast, in the endoscope system (the image analysis system) of the fifth embodiment, a distribution characteristic value of luminance values equal to or lower than a reference value is extracted in obtained distribution characteristic values.

When, for example, scattering of glucose is performed as the load (the predetermined action) to the subject, the blood flow rate tends to increase after the scattering of glucose rather than before the scattering, so that an entirely dark image may be generated.

In contrast, by use of the property in which increase change of an image luminance value is easily influenced by halation at a time of photographing the image or the property in which eyes of human beings are sensitive to change "from a bright condition to a dark condition" but are insensitive to change "from a dark condition to a bright condition", the fifth embodiment in view of the aforementioned circumstance, focuses on the decrease change of a luminance value of distribution characteristics, so that the following configuration is used.

Figure 24:
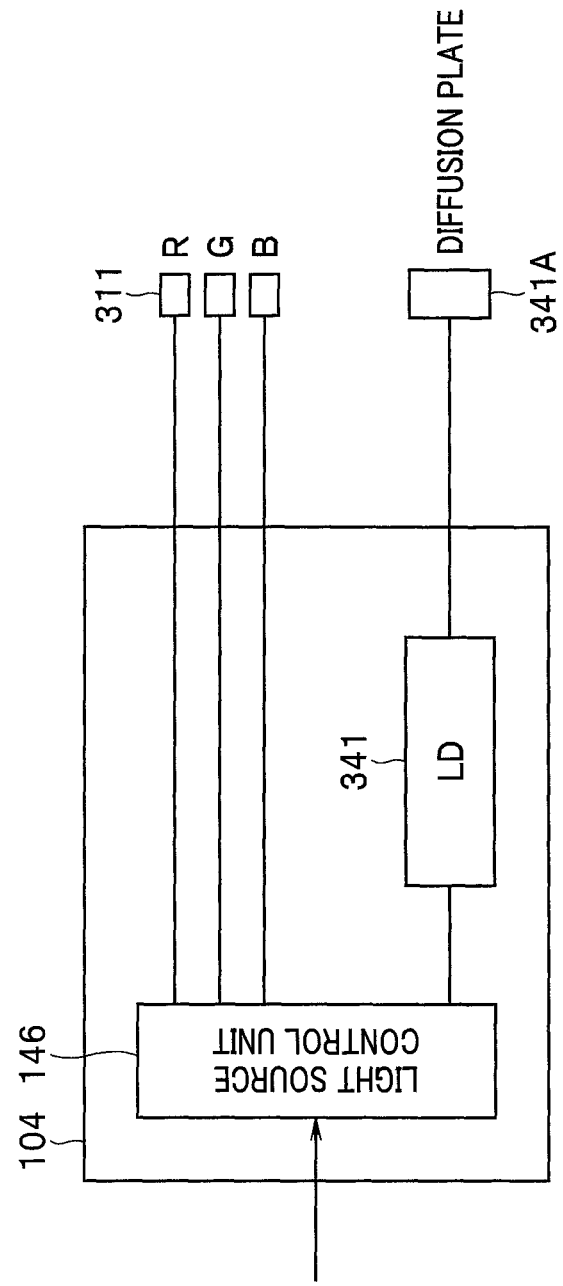
FIG. 24 is a block diagram illustrating another modification of the light source apparatus in the image analysis system according to any one of the first, second, and fourth to seventh embodiments of the present invention.

That is, in calculation of the distribution characteristic value of the luminance values of each analysis target region obtained by the region extraction unit 33 in the image analysis apparatus (the video processor 3) of the fifth embodiment, a predetermined reference value is defined for luminance values and the distribution characteristic value equal to or lower than the reference value is extracted (see FIG. 24).

In the present embodiment, the predetermined reference value for luminance values is a value obtained from the median or the average value of the luminance values, or the peak value of the luminance values, for example.

<Image Analysis in the Fifth Embodiment>

FIG. 21 is a flowchart showing an image analysis process to be executed by the image analysis apparatus in the image analysis system according to the fifth embodiment.

In the fifth embodiment, as shown in FIG. 21, the color component value extraction unit 36 of the distribution characteristic value calculation unit 34 extracts, at step S17 after steps S10 to S16, the color component values, for example, R, B, G component values of each of pixels configuring the analysis target region OR (step S17), as in the first embodiment.

That is, the color component value extraction unit 36 extracts the respective color component values (R, G, B component values) of each of pixels configuring the analysis target region OR in the first image extracted by the region extraction unit 33, and the respective color component values (R, G, B component values) of each of pixels configuring the analysis target region OR in the second image.

Thereafter, when the total luminance value calculation unit 37 of the distribution characteristic value calculation unit 34 calculates the total luminance value (the first total luminance value) of the respective color component values concerning the first image which are extracted by the color component value extraction unit 36 and the total luminance value (the second total luminance value) of the respective color component values concerning the second image which are extracted by the color component value extraction unit 36, luminance values equal to or lower than a predetermined reference value are extracted, as shown in FIG. 22.

The luminance-value distribution characteristic value calculation unit 38 of the distribution characteristic value calculation unit 34 calculates, for each of the first total luminance value and the second total luminance value, a distribution characteristic value of the "luminance values equal to or lower than the reference value" which are extracted by the total luminance value calculation unit 37 (step S18B).

Thereafter, as in the first embodiment, the image analysis unit 35 of the fifth embodiment calculates, as the amount of change in the distribution characteristic value of the post-load image with respect to the prior-to-load image, the amount of change in the distribution characteristic value of the "luminance values equal to or lower than the reference value" which are calculated by the luminance-value distribution characteristic value calculation unit 38 (step S19).

As described above, the fifth embodiment provides an effect the same as the effect by the first embodiment, and also, can exclude luminance values at luminance levels not appropriate for evaluation, whereby a more accurate analysis result can be obtained.

Sixth Embodiment

Next, a sixth embodiment of the present invention is described.

An endoscope system (an image analysis system) according to the sixth embodiment has basic components identical to the components of the first embodiment. Thus, only the difference from the first embodiment is described and a description of other details is omitted.

As described above, in the first embodiment, when the amount of change in the distribution characteristic value of the luminance values is calculated as the degree of change of the post-load image with respect to the prior-to-load image (see step S19 in FIG. 5), the amount of change is obtained by:

$$\text{amount of change} = <2> - <1> \qquad \text{[Equation 1]}$$

wherein <1> represents the first distribution characteristic value concerning the first image (the prior-to-load image) and <2> represents the second distribution characteristic value concerning the second image (the post-load image).

When scattering of glucose is applied as the load (the predetermined action) to be imparted to the subject, the distribution characteristic value as a standard deviation in the second image acquired after scattering of glucose is likely to be higher than the distribution characteristic value of the first image acquired before the scattering, according to the condition.

In view of the circumference, in the sixth embodiment, a coefficient $\alpha$ and a coefficient $\beta$ are provided to the distribution characteristic value of the luminance values of each analysis target region in the first image and the distribution characteristic value of the luminance values of each analysis target region in the second image, respectively. Thus, in calculation of the amount of change in the distribution characteristic value, the image analysis unit 35 obtains the amount of change by:

$$\text{amount of change} = \beta \times <2> - \alpha \times <1> \qquad \text{[Equation 2]}$$

wherein <1> represents the first distribution characteristic value concerning the first image and <2> represents the second distribution characteristic value concerning the second image, respectively.

Since a standard deviation as the distribution characteristic value is likely to be higher in the second image obtained after scattering of glucose than in the first image obtained before the scattering, as described above, the coefficients $\alpha$, $\beta$ may be set to satisfy:

$$\beta \geq \alpha.$$

As described above, the endoscope system (the image analysis system) of the sixth embodiment can provide, even when the difference between the first distribution characteristic value <1> concerning the first image and the second distribution characteristic value <2> concerning the second image is small, a more characteristic result can be obtained by multiplication with the coefficients which are defined by:

$$\beta \geq \alpha.$$

Seventh Embodiment

Next, a seventh embodiment of the present invention is described.

An endoscope system (an image analysis system) according to the seventh embodiment has basic components identical to the components of the first embodiment. Thus, only the difference from the first embodiment is described and a description of other details is omitted.

As described above, in the first embodiment, the "amount of change" in the distribution characteristic value of the luminance values is calculated as the degree of change of the post-load image with respect to the prior-to-load image.

In contrast, the seventh embodiment focuses on, as the degree of change of the post-load image with respect to the prior-to-load image, the "rate of change" in the distribution characteristic value of the luminance values.

More specifically, in the seventh embodiment, the image analysis unit 35 calculates the rate of change by:

$$\text{rate of change} = (<2> - <1>)/(<1> + <2>) \qquad \text{[Equation 3]}$$

wherein <1> represents the first distribution characteristic value concerning the first image and <2> represents the second distribution characteristic value concerning the second image.

As described above, according to the endoscope system (the image analysis system) of the seventh embodiment, the rate of change is calculated as the degree of change of the post-load image with respect to the prior-to-load image, so that an influence of variation in the distribution characteristic value concerning the prior-to-load image as the first image can be canceled. As a result, the seventh embodiment provides an effect that comparison of the degree of change in the distribution characteristic value can be more accurately performed even for different cases of diseases.

The image analysis apparatus (or the image analysis system, this applies hereinafter) has been mainly described above. However, the seventh embodiment may be an operation method for operating the image analysis apparatus in the aforementioned manner, a processing program for causing a computer to execute the same process as the process to be executed by the image analysis apparatus, a non-temporal recording medium readable by a computer having the process program recorded in the medium, or the like.

The endoscope systems of the first to third and fifth to seventh embodiments each use a so-called frame-sequential method. However, these endoscope systems are not limited to a frame-sequential method, but are applicable to a so-called simultaneous-type observation method.

Figure 23:
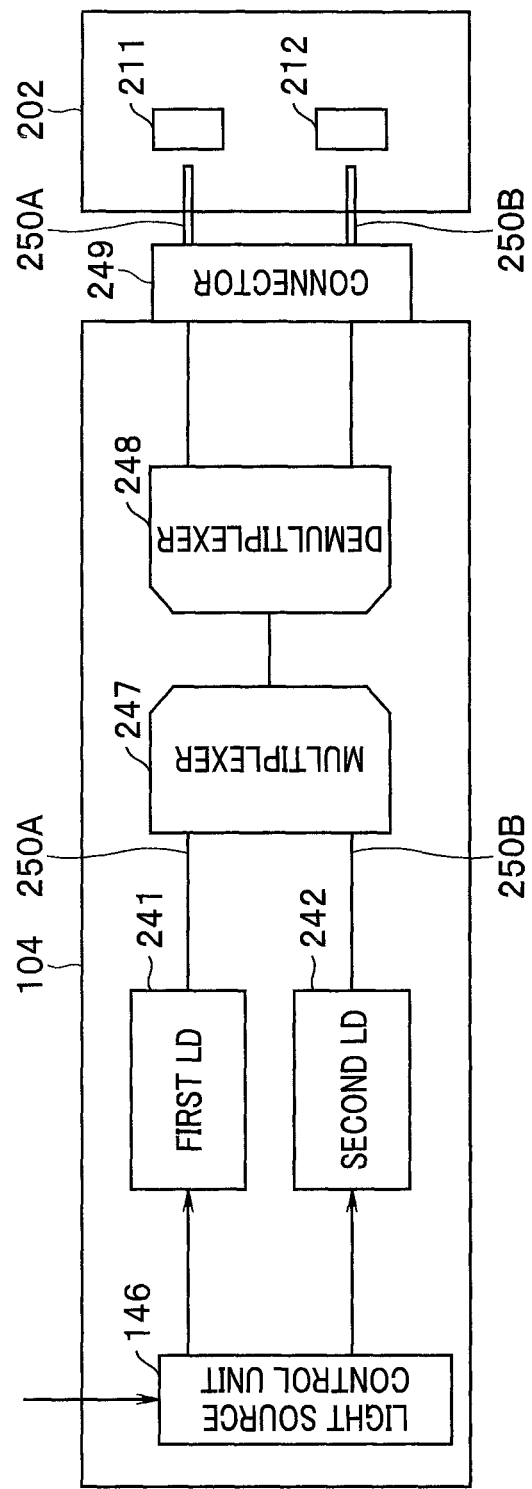
FIG. 23 is a block diagram illustrating one modification of a light source apparatus in the image analysis system according to any one of the first, second, and fourth to seventh embodiments of the present invention.

Moreover, the endoscope systems of the aforementioned first, second, and fourth to seventh embodiments each use an observation method using narrow band light such as NBI, but are not limited to the method. The endoscope systems of the first, second, and fourth to seventh embodiments are applicable to observation with white light, observation as shown in FIG. 23 in which light for use as an observation light is obtained by multiplexing laser lights 250A, 250B from a first LD 241, a second LD 242 by use of a combiner 247 which is a multiplexer, demultiplexing the multiplexed light by use of a coupler 248 which is a demultiplexer, and applying the demultiplexed light to phosphors 211, 212 provided to an endoscope 202 connected via a connector 249, etc., or observation as shown in FIG. 24 in which a combination of a laser light source 341 and a diffusion plate 341A, and respective RGB light emitting diodes 311 are provided, or the like. Thus, the endoscope systems are applicable to observation that provides the equivalent effect irrespective of a light source.

In each of the endoscope systems of the first to seventh embodiments, an observation target can be observed in detail by combination with magnifying observation. However, the endoscope systems are not limited to the observation, but are applicable even to observation at a normal magnification.

The present invention is not limited to the aforementioned embodiments exactly as they are. At a stage of carrying out the embodiments, the embodiments can be embodied with the component elements modified within the range of the gist of the embodiments. Further, by an appropriate combination of a plurality of the component elements disclosed in the aforementioned embodiments, various aspects of the invention can be formed. For example, some of the elements shown in the embodiments may be omitted. Moreover, some of the component elements may be combined with one another across the different embodiments. As such, various modification or application can be reasonably made within a range not departing from the gist of the invention.

What is claimed is:

1. An image analysis apparatus comprising:
a processor configured to:
receive an input of a first image of a subject acquired at a first timing and an input of a second image of the subject acquired at a second timing later than the first timing, in a state where an endoscope is continuously inserted in the subject;
determine, as analysis target regions, respective predetermined regions in the first image and the second image acquired at timings before and after execution of a predetermined action to the subject;
obtain a first distribution characteristic value by extracting a color component of the analysis target region in the first image, and to obtain a second distribution characteristic value by extracting a color component of the analysis target region in the second image; and
calculate a degree of change in the second distribution characteristic value with respect to the first distribution characteristic value.

2. The image analysis apparatus according to claim 1, wherein the predetermined action is administration of a medicinal solution to the subject.

3. The image analysis apparatus according to claim 1, wherein each of the first and second distribution characteristic values is a standard deviation or dispersion of the color component of the corresponding analysis target region.

4. The image analysis apparatus according to claim 1, wherein the processor is configured to:
set a predetermined reference value for the analysis target region in each of the first and second images in accordance with a distribution characteristic of the color component; and
further obtain the first and second distribution characteristic values of a value lower than the reference value.

5. The image analysis apparatus according to claim 1, wherein the processor is configured to:
extract, from each of the first and second images, a predetermined number of elements each formed of an annular surrounding portion and a center portion surrounded by the annular surrounding portion and colored in a color different from the color of the annular surrounding portion; and
determine the center portions of the predetermined number of extracted elements as the analysis target regions.

6. The image analysis apparatus according to claim 5, wherein the processor is configured to:
detect, in each of the first and second images, an edge forming a closed curve, and determine whether or not the size of a portion surrounded by the detected edge forming the closed curve falls within a range that can be taken by the analysis target region; and
specify, as the analysis target region, an inside of a region surrounded by the edge forming the closed curve, when the portion surrounded by the edge forming the closed curve falls within the range that can be taken by the analysis target and when the inside and an outside of the portion surrounded by the edge forming the closed curve are colored in different colors.

7. The image analysis apparatus according to claim 5, wherein the elements are included in an intestinal villus image part, and
wherein the processor is configured to:
extract, from each of the first and second images, the predetermined number of elements of interest each including an image part where a mucous epithelium formed on a surface of the intestinal villus is shown as the annular surrounding portion and an image part where an area surrounded by the mucous epithelium is shown as the center portion colored in the color different from the color of the mucous epithelium; and
determine, as the analysis target regions, the center portions of the predetermined number of extracted elements of interest.

8. The image analysis apparatus according to claim 1, wherein the first and second images are each obtained by picking up an image of reflection light generated upon illumination of the subject by means of the endoscope with illumination light of a predetermined frequency band.

9. The image analysis apparatus according to claim 1, wherein the processor is configured to obtain the first and second distribution characteristic values based on red components, blue components, and green components of the first and second images.

10. The image analysis apparatus according to claim 1, wherein the processor is configured to determine one or more of the analysis target regions from among, in the entire first and second images, appropriate luminance regions each average luminance of which falls within in an appropriate luminance range appropriate for extraction of a color component value, the average luminance being calculated for each predetermined-sized region.

11. The image analysis apparatus according to claim 10, wherein the processor is configured to extract the analysis target regions by excluding an inappropriate region which is inappropriate for extraction of a color component value.

12. The image analysis apparatus according to claim 1, wherein, when the first distribution characteristic value is defined as <1>, the second distribution characteristic value is defined as <2 >, coefficients are defined as α and β, and β≥α, the amount of change is calculated by:

amount of change=β×<2>−α×<1>.

13. The image analysis apparatus according to claim 1, wherein, when the first distribution characteristic value is defined as <1>and the second distribution characteristic value is defined as <2>, the amount of change is calculated by:

rate of change=(<2>−<1>)/(<1>+<2>).

14. An image analysis system comprising:
the endoscope; and
the image analysis apparatus according to claim 1.

15. A method for operating an image analysis apparatus, the method comprising:
- inputting, to a processor, a first image of a subject acquired at a first timing and a second image of the subject acquired at a second timing later than the first timing in a state where an endoscope is continuously inserted in the subject;
- determining, by the processor, respective predetermined regions in the first image and the second image as analysis target regions, the first and second images being acquired at timings before and after execution of a predetermined action to the subject;
- obtaining, by the processor, a first distribution characteristic value by extracting a color component of the analysis target region in the first image and obtaining, by the processor, a second distribution characteristic value by extracting a color component of the analysis target region in the second image; and
- calculating, by the processor, a degree of change of the second distribution characteristic value with respect to the first distribution characteristic value.

* * * * *

UNITED STATES PATENT AND TRADEMARK OFFICE
CERTIFICATE OF CORRECTION

PATENT NO. : 10,572,755 B2
APPLICATION NO. : 15/936857
DATED : February 25, 2020
INVENTOR(S) : Momoko Yamanashi et al.

It is certified that error appears in the above-identified patent and that said Letters Patent is hereby corrected as shown below:

On the Title Page

Item (54) should read:
IMAGE ANALYSIS APPARATUS FOR CALCULATING DEGREE OF CHANGE IN DISTRIBUTION CHARACTERISTIC VALUES, IMAGE ANALYSIS SYSTEM, AND METHOD FOR OPERATING IMAGE ANALYSIS APPARATUS Signed and Sealed this
Fifteenth Day of September, 2020

Andrei Iancu
*Director of the United States Patent and Trademark Office*